(12) United States Patent
Han et al.

(10) Patent No.: US 11,389,670 B2
(45) Date of Patent: Jul. 19, 2022

(54) SYSTEMS AND METHODS FOR QUALITY ASSURANCE OF RADIATION THERAPY

(71) Applicant: SHANGHAI UNITED IMAGING HEALTHCARE CO., LTD., Shanghai (CN)

(72) Inventors: Wei Han, Shanghai (CN); Zhao Jin, Shanghai (CN); Yanfang Liu, Shanghai (CN); Wei Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 268 days.

(21) Appl. No.: 16/729,308

(22) Filed: Dec. 28, 2019

(65) Prior Publication Data

US 2020/0206539 A1 Jul. 2, 2020

(30) Foreign Application Priority Data

Dec. 29, 2018 (CN) .......................... 201811634279.3

(51) Int. Cl.
*A61N 5/10* (2006.01)

(52) U.S. Cl.
CPC .......... *A61N 5/1071* (2013.01); *A61N 5/1031* (2013.01); *A61N 5/1075* (2013.01); *A61N 5/1081* (2013.01); *A61N 2005/1034* (2013.01)

(58) Field of Classification Search
CPC ...... A61N 5/10–1084; A61N 2005/1085–1098
See application file for complete search history.

(56) References Cited

U.S. PATENT DOCUMENTS

| 9,089,696 | B2 | 7/2015 | Verhaegen et al. | |
|---|---|---|---|---|
| 9,242,120 | B2 | 1/2016 | Verhaegen et al. | |
| 2009/0129659 | A1* | 5/2009 | Deutschmann | A61N 5/1048 382/132 |
| 2016/0136459 | A1 | 5/2016 | Verhaegen et al. | |

(Continued)

FOREIGN PATENT DOCUMENTS

| CN | 1724089 A | 1/2006 |
|---|---|---|
| JP | 2017189527 A | 10/2017 |

OTHER PUBLICATIONS

Siebers, Jeffrey V. et al., Monte Carlo computation of dosimetric amorphous silicon electronic penal images, Medical Physics, 31(7): 2135-2146, 2004.

(Continued)

*Primary Examiner* — Thaddeus B Cox
(74) *Attorney, Agent, or Firm* — Metis IP LLC

(57) ABSTRACT

Systems and methods for a pre-treatment quality assurance (QA) of a radiotherapy device may be provided. The method may include determining a measured dose image through an electronic portal dose imaging device (EPID). The method may include determining an energy fluence distribution map related to radiation beams predicted by a first portal dose prediction model. The method may include determining a predicted dose image based on the energy fluence distribution map and a simulated energy response curve related to the EPID. The method may further include determining differences between the measured and predicted dose images by comparing the dose distributions of the measured and predicted dose images.

20 Claims, 12 Drawing Sheets

(56) References Cited

U.S. PATENT DOCUMENTS

2017/0177812 A1 6/2017 Sjölund
2018/0243586 A1* 8/2018 Ramezanzadeh Moghadam ........ G16H 20/40

OTHER PUBLICATIONS

First Office Action in Chinese Application No. 201811634279.3 dated Apr. 3, 2020, 10 pages.

* cited by examiner

SYSTEMS AND METHODS FOR QUALITY ASSURANCE OF RADIATION THERAPY

CROSS-REFERENCE OF RELATED APPLICATIONS

This application claims priority of Chinese Patent Application No. 201811634279.3, filed on Dec. 29, 2018, the contents of which are hereby incorporated by reference.

TECHNICAL FIELD

The disclosure generally relates to radiation therapy technique, and more particularly relates to systems and methods for pre-treatment quality assurance (QA) of a radiotherapy device.

BACKGROUND

In order to achieve precise radiation therapy and improve the efficiency of tumor treatment, an image-guided radiation therapy (IGRT) apparatus is widely used in clinical applications. In the IGRT apparatus, an electronic portal imaging device (EPID) is an imaging component for accurately locating the tumor before or during the radiation treatment. According to an image (e.g., a portal image or a portal dose image) acquired by the EPID, a doctor can determine whether a subject's position is accurate, and whether the location or shape of the tumor has changed, so as to reduce the possibility of irradiating normal tissues and achieve precise radiation treatment.

In radiation therapy (hereinafter referred to as radiotherapy), a treatment plan system (TPS) can be used to predetermine a treatment plan before the treatment commences. To achieve precise radiotherapy, the accuracy in delivering a planned radiation dose to the subject based on the predetermined treatment plan needs to be verified. Some quality assurance (QA) tools and protocols are needed to verify that the planned radiation dose is delivered to the subject. For example, conventional films and/or dose map detectors are used to perform the pre-treatment QA verification. Compared with the conventional films and the dose map detectors, the use of the EPID may save the time of the pre-treatment QA verification and improve the verification efficiency. Therefore, it is desirable to develop systems and methods for quality assurance of radiation therapy using the EPID.

SUMMARY

In a first aspect of the present disclosure, a system is provided. The system may include at least one storage device storing a set of instructions and at least one processor in communication with the at least one storage device. When executing the set of instructions, the at least one processor may direct the system to perform one or more operations as the following. The at least one processor may determine a measured dose image through an electronic portal dose imaging device (EPID). The measured dose image may be indicative of a dose distribution of radiation beams measured by the EPID, and the measured radiation beams may correspond to a planned radiation dose and a planned gantry angle. The at least one processor may determine an energy fluence distribution map related to radiation beams predicted by a first portal dose prediction model. The predicted radiation beams may correspond to the planned radiation dose and the planned gantry angle. The at least one processor may determine a predicted dose image based on the energy fluence distribution map and a simulated energy response curve related to the EPID. The predicted dose image may be indicative of a dose distribution of the predicted radiation beams. The at least one processor may determine differences between the measured and predicted dose images by comparing the dose distributions of the measured and predicted dose images.

In some embodiments, the at least one processor may obtain a plurality of raw images with respect to the measured radiation beams through the EPID. The at least one processor may obtain one or more calibration parameters. The at least one processor may calibrate, based on the one or more calibration parameters, each of the plurality of raw images. The at least one processor may form a final calibrated image based on the plurality of calibrated raw images. The at least one processor may convert the final calibrated image to the measured dose image.

In some embodiments, the at least one processor may obtain a plurality of raw images with respect to the measured radiation beams through the EPID. The at least one processor may obtain one or more calibration parameters. The at least one processor may summarize the plurality of raw images. The at least one processor may form a final calibrated image by calibrating, based on the one or more calibration parameters, the summarized raw image. The at least one processor may convert the final calibrated image to the measured dose image.

In some embodiments, the one or more calibration parameters may include at least one of a position offset value, a detector gain value, or a curve correction value.

In some embodiments, the at least one processor may determine the position offset based on position deviations of first measured flood-field images relative to a center of the EPID. The at least one processor may determine the detector gain value based on a second measured flood-field image and a beam profile value. The at least one processor may determine the curve correction value based on a third measured flood-field image and a predicted flood-field image. The third measured flood-field image may be associated with the second measured flood-field image, and the predicted flood-field image may be generated using a second portal dose prediction model.

In some embodiments, the first portal dose prediction model or the second portal dose prediction model may include a Monte Carlo (MC) simulation model.

In some embodiments, the at least one processor may correct a predicted output factor of the first portal dose prediction model based on an output correction factor. The at least one processor may determine the energy fluence distribution map by feeding the corrected output factor to the first portal dose prediction model.

In some embodiments, the at least one processor may determine an intermediate predicted dose image based on the energy fluence distribution map and the simulated energy response curve. The at least one processor may determine the predicted dose image by correcting the intermediate predicted dose image using an absolute dose correction factor.

In some embodiments, the simulated energy response curve related to the EPID may be determined in advance by modeling an energy deposition efficiency of the EPID.

In a second aspect of the present disclosure, a method is provided. The method may include one or more operations. The one or more operations may be implemented on a computing device having at least one processor and at least one storage device. The at least one processor may determine a measured dose image through an electronic portal dose imaging device (EPID). The measured dose image may be indicative of a dose distribution of radiation beams measured by the EPID, and the measured radiation beams may correspond to a planned radiation dose and a planned gantry angle. The at least one processor may determine an energy fluence distribution map related to radiation beams predicted by a first portal dose prediction model. The predicted radiation beams may correspond to the planned radiation dose and the planned gantry angle. The at least one processor may determine a predicted dose image based on the energy fluence distribution map and a simulated energy response curve related to the EPID. The predicted dose image may be indicative of a dose distribution of the predicted radiation beams. The at least one processor may determine differences between the measured and predicted dose images by comparing the dose distributions of the measured and predicted dose images.

In a third aspect of the present disclosure, a non-transitory computer-readable medium is provided. The non-transitory computer-readable medium includes at least one set of instructions. When the at least one set of instructions are executed by at least one processor of a computer device, the at least one set of instructions directs the at least one processor to perform one or more operations as the following. The at least one processor may determine a measured dose image through an electronic portal dose imaging device (EPID). The measured dose image may be indicative of a dose distribution of radiation beams measured by the EPID, and the measured radiation beams may correspond to a planned radiation dose and a planned gantry angle. The at least one processor may determine an energy fluence distribution map related to radiation beams predicted by a first portal dose prediction model. The predicted radiation beams may correspond to the planned radiation dose and the planned gantry angle. The at least one processor may determine a predicted dose image based on the energy fluence distribution map and a simulated energy response curve related to the EPID. The predicted dose image may be indicative of a dose distribution of the predicted radiation beams. The at least one processor may determine differences between the measured and predicted dose images by comparing the dose distributions of the measured and predicted dose images.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
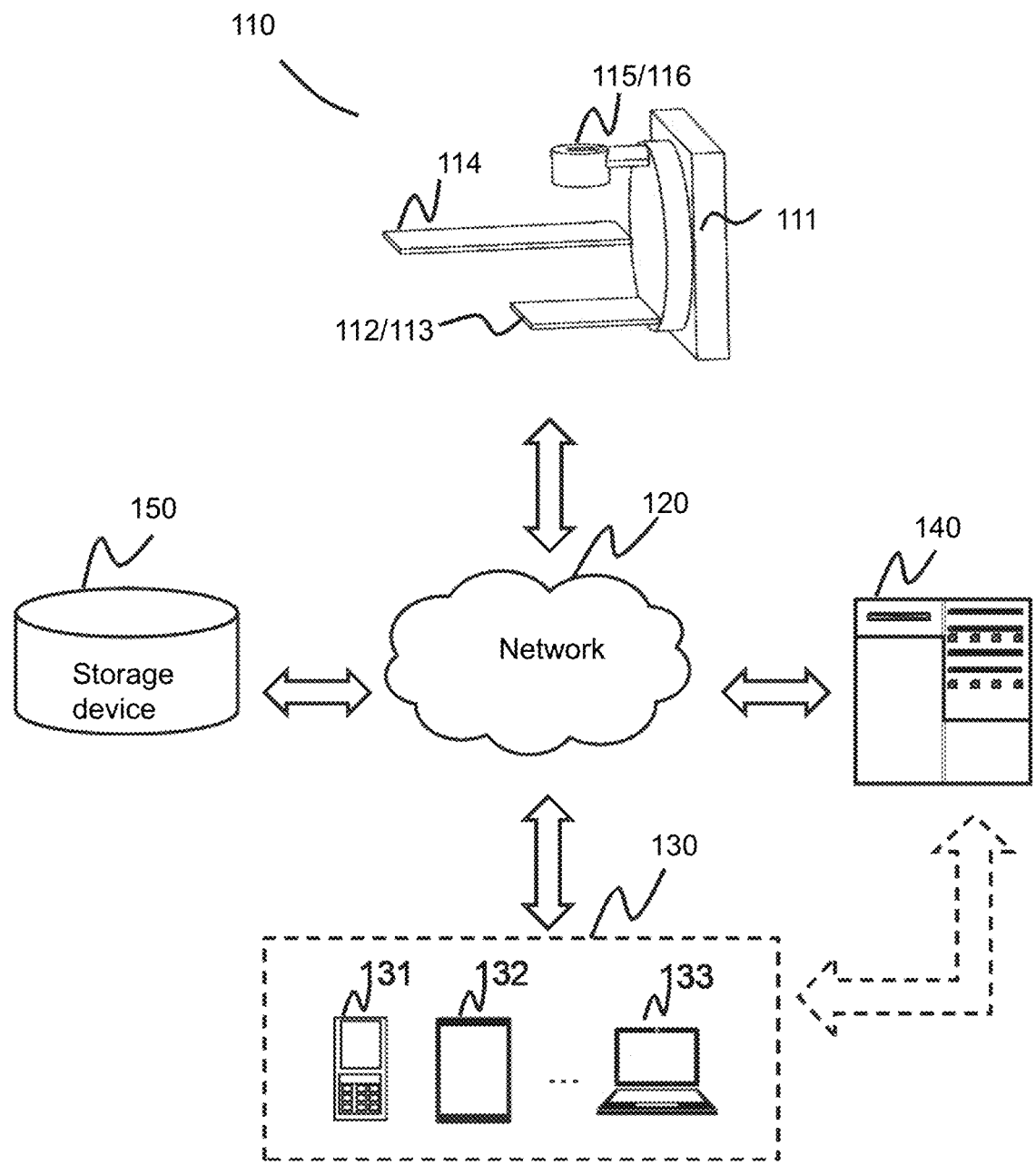
FIGS. 1 and 2 illustrate an exemplary medical system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Various embodiments of the systems and methods described in the present disclosure may be used for quality assurance (QA) of radiation treatment and/or verifying a predetermined treatment plan. The system may determine dose differences between the planned radiation dose distribution and the actual radiation dose distribution (i.e., the actual dose delivered to a subject (e.g., a patient) during the radiation treatment). In some embodiments, the system may determine the dose differences by comparing a predicted dose image and a measured dose image. The predicted dose image may be generated by a portal dose prediction model (e.g., a Monte Carlo (MC) simulation model). The portal dose prediction model may simulate the radiation delivery between a treatment head and an EPID of an IGRT apparatus and generate the predicted dose image. In some embodiments, the system may generate an energy fluence distribution map related to radiation beams predicted (or simulated) by the first portal dose prediction model. The system may determine the predicted dose image based on the energy fluence distribution map and a simulated energy response curve related to the EPID. The predicted dose image may be indicative of a predicted dose distribution of the predicted radiations. In some embodiments, the system may measure an actual dose image (i.e., the measured dose image) through the EPID. For example, in accordance with the same planned radiation dose and gantry angle, the treatment head may deliver the radiations onto the EPID. The EPID may be configured to acquire image data to generate the measured dose image. The measured dose image may be indicative of a dose distribution of the measured radiations (i.e., actual radiations). The system may compare the dose distributions of the measured and the predicted dose images to evaluate radiation delivery deviation or errors (e.g., dose differences between the predicted dose distribution and the measured dose distribution). Then whether the planned treatment plan is reasonable may be evaluated based on the dose differences.

With reference to the systems and methods described in the present disclosure, the predicted dose image may be determined based on the energy fluence distribution map and the simulated energy response curve. The system may not only predict the dose distribution of the planned radiation dose accurately, but also reduce or avoid complex particles (e.g., photons of the radiation beam) transport simulation of conventional MC simulation algorithms. Therefore, the computational efficiency of the system may be improved.

Figure 2:
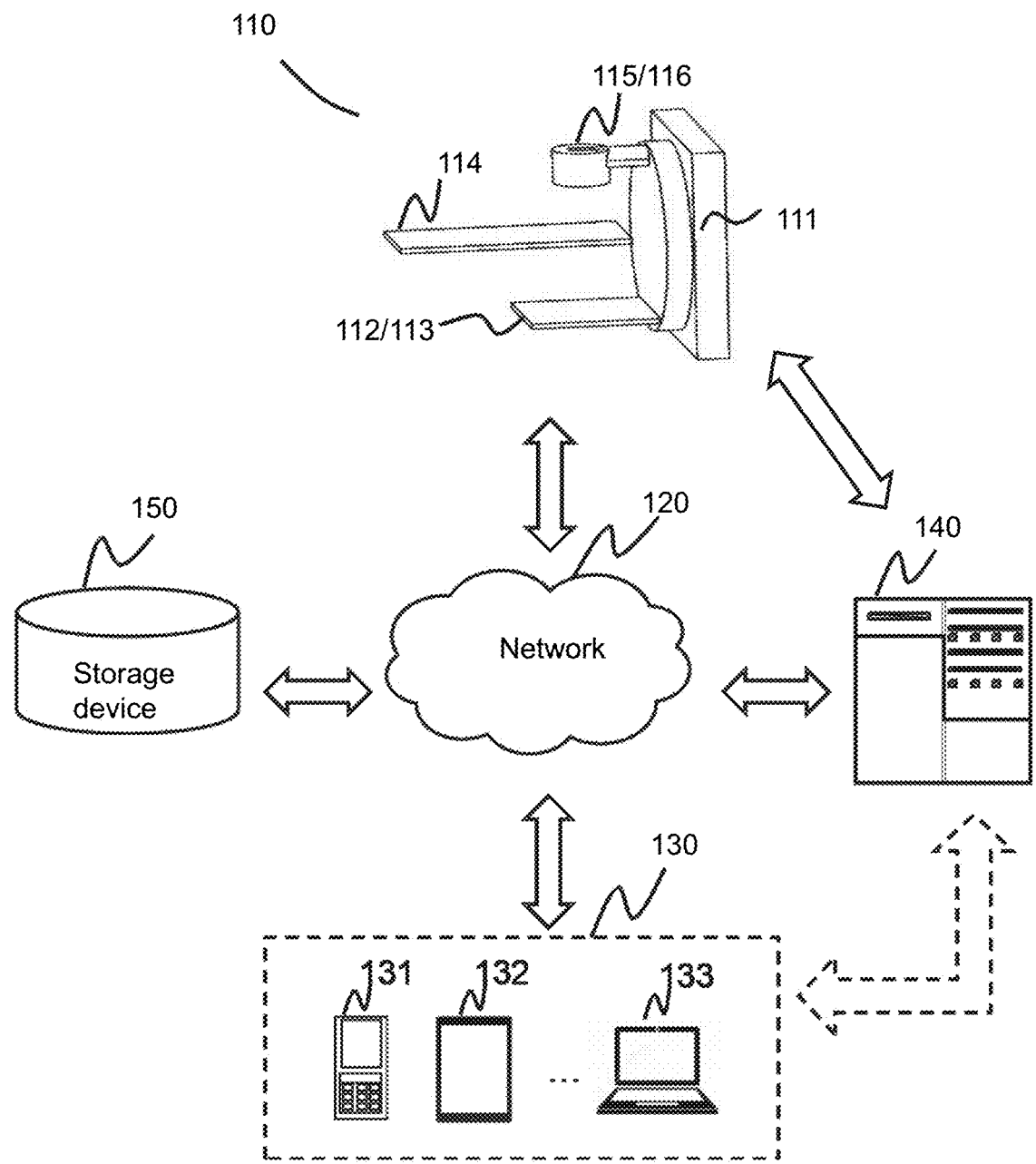

FIGS. 1 and 2 illustrate an exemplary medical system according to some embodiments of the present disclosure. As illustrated in FIG. 1 or FIG. 2, the medical system 100 may include an image-guided radiation therapy (IGRT) apparatus 110, a network 120, one or more terminals 130, a processing device 140, and a storage device 150. The components in the medical system 100 may be connected in one or more of various ways. Merely by way of example, as illustrated in FIG. 1, the IGRT apparatus 110 may be connected to the processing device 140 through the network 120. As illustrated in FIG. 2, the IGRT apparatus 110 may be directly connected to the processing device 140 (as indicated by the bi-directional arrow in a solid line linking the IGRT apparatus 110 and the processing device 140). As another example, the one or more terminals 130 may be connected to the processing device 140 directly (as indicated by the bi-directional arrow in dotted lines linking the one or more terminals 130 and the processing device 140) or through the network 120, as illustrated in FIG. 1 or FIG. 2.

The IGRT apparatus 110 may be a single-modality device and/or a multi-modality (e.g., dual-modality) device that can generate a medical image and perform a radiation therapy (e.g., based on the medical image of a region of interest (ROI)). In some embodiments, the medical image may be generated by an imaging component (also referred to as imaging device) of the IGRT apparatus 110. Exemplary imaging devices may include a computed tomography (CT) device, a single photon emission computed tomography (SPECT) device, a multi-modality imaging device, or the like, or any combination thereof. Exemplary CT device may include a cone beam computed tomography (CBCT) device. Exemplary multi-modality imaging devices may include a computed tomography-positron emission tomography (CT-PET) device, a computed tomography-magnetic resonance imaging (CT-MRI) device, or the like. The radiation therapy may be performed by a radiotherapy component (also referred to as radiotherapy (RT) device) of the IGRT apparatus 110. Exemplary RT devices may include a linear accelerator (LINAC), a Co-60 gamma radiator, or the like.

The "image" mentioned in the present disclosure may refer to a two-dimensional (2D) image, a three-dimensional (3D) image, a four-dimensional (4D) image (e.g., a video, a time series of 3D images), and/or image related data (e.g., CT data, projection data corresponding to the CT data, etc.).

The IGRT apparatus 110 may include one or more diagnostic devices and/or therapeutic devices, such as a CT device, a PET-CT device, a volume CT device, an RT device, or the like.

In some embodiments, the IGRT apparatus 110 may only include the RT device (e.g., the LINAC). As illustrated in FIG. 1, the RT device may include a gantry 111, a treatment table 114, a treatment head 116, and an electron portal imaging device (EPID) 113. The gantry 111 may support the treatment head 116 and the EPID 113, and move (e.g., translate and/or rotate) these devices to various rotational and/or axial positions relative to a subject (e.g., a patient, a man-made object, a specific organ or tissues) to be examined. The subject to be examined (e.g., to be imaged and/or treated) may be placed on the treatment table 114. The gantry 111 may be a ring gantry, but other types of mounting arrangements may also be employed. For example, a C-type, a partial ring gantry, or a robotic arm can be used.

The treatment head 116 of the RT device may include a target, a primary collimator, a flattening filter, Y jaws, X jaws, and a Multi-leaf Collimator (MLC), and so on. Accelerated particles (e.g., electrons) may strike the target to produce radiation beams (e.g., photon beams or X-ray beams). The radiation beams may pass through the one or more components (e.g., the primary collimator, the flattening filter, the Y jaws, X jaws, and the MCL) of the treatment head 116 to form desired radiation beams with a certain shape, which corresponds to a shape and size of a region of interest (ROI) in a subject (e.g., a lesion in the subject). The radiation beams may be irradiated to the ROI for the radiation therapy. In some embodiments, the radiation beams may impinge on the EPID 113 after passing through the ROI. The EPID 113 may acquire a portal image for verifying a position of the subject, or a portion thereof (e.g., the position of the ROI in the subject), and a field size.

In some embodiments, as illustrated in FIG. 1, the IGRT apparatus 110 may include a CBCT device and an RT device. For example, the IGRT apparatus 110 may include the gantry 111, the treatment table 114, a scan source 115, the treatment head 116, the detector 112, and the EPID 113. The gantry 111 may be configured to support the scan source 115, the treatment head 116, the detector 112, the EPID 113, and so on. The gantry 111 may move (e.g., translate and/or rotate) these devices to various circumferential and/or axial positions relative to the subject to be examined. The subject to be examined may be placed on the treatment table 114. The scan source 115 of the CBCT device and the treatment head 116 of the RT device may be integrated or disposed separately. For example, the scan source 115 and the treatment head 116 can be integrated to a same apparatus (e.g., two radiation sources implemented in the same apparatus, or one radiation source that can emit radiation beams of different energy levels for imaging and treatment, respectively), and they are disposed at the same location, as illustrated in FIG. 1 or FIG. 2. As another example, the scan source 115 and the treatment head 116 may also be disposed separately, and they are disposed at different locations on the gantry 111, not shown in FIG. 1 or FIG. 2. In some embodiments, the scan source 115 may emit a cone X-ray beam toward the subject placed on the treatment table 114. The X-rays may be attenuated when passing through the subject. The detector 112 of the CBCT device may detect at least a portion of the attenuated X-rays. The CBCT device may generate image data based on the attenuated X-rays detected by the detector 112.

In some embodiments, the detector 112 of the CBCT device and the EPID 113 of the RT device may be integrated or disposed separately. For example, the detector 112 and the EPID 113 can be integrated to a same apparatus, and disposed at the same location, as illustrated in FIG. 1 or FIG. 2. As another example, the detector 112 and the EPID 113 may be disposed separately, and they are disposed at different locations on the gantry 111, not shown in FIG. 1 or FIG. 2.

In some embodiments, the locations of the scan source 115 and the detector 112 of the CBCT device can be disposed oppositely such that the detector 112 may receive the imaging radiation beams from the scan source 115. The treatment head 116 and EPID 113 of the RT device can be disposed oppositely such that the EPID 113 may receive the treatment radiation beams from the treatment head 116.

The network 120 may include any suitable network that can facilitate the exchange of information and/or data. In some embodiments, one or more components of the medical system 100 (e.g., the CBCT device, the RT device, the terminal(s) 130, the processing device 140, the storage device 150, etc.) may communicate with each other via the network 120. For example, the processing device 140 may acquire image data from the CBCT device and/or the RT device via the network 120. As another example, the processing device 140 may acquire projection data (e.g., subject-related projection data) from the CBCT device and/or the RT device over the network 120. As a further example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The one or more terminals 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include smart lighting apps, smart appliance control apps, smart monitoring apps, smart TVs, smart cameras, walkie-talkies, or the like, or any combination thereof. In some embodiments, the wearable device may include a wristband, footwear, glasses, a helmet, a watch, a garment, a backpack, a smart accessory or the like, or any combination thereof. In some embodiments, the mobile device may include a mobile phone, a personal digital assistant (PDA), a game device, a navigation device, a point of sale (POS) device, a laptop computer, a tablet computer, a desktop computer, or the like, or any combination thereof. In some embodiments, the virtual reality device and/or the augmented reality apparatus may include a virtual reality helmet, virtual reality glasses, a virtual reality eyewear, an augmented reality helmet, augmented reality glasses, an augmented reality eyewear, or the like, or any combination thereof. For example, the virtual reality device and/or the augmented reality device may include a Google Glass™, an Oculus Rift™, a Hololens™, a Gear VR™, etc. In some embodiments, the one or more terminals 130 may be part of the processing device 140.

The processing device 140 may process data and/or information obtained from the IGRT apparatus 110, the one or more terminals 130, the storage device 150, or other components of the medical system 100. For example, the obtained data and/or information may include imaging data related to the subject.

In some embodiments, the processing device 140 may process the radiation data and the attenuation coefficient distribution related to the subject to determine composite image data after the radiation beam has passed through the subject. The imaging data may include the energy response data generated after the composite image data is projected onto the detector. The processing device 140 may determine an energy response function of the detector 112 and/or the EPID 113 based on the imaging data and the composite image data.

In some embodiments, the processing device 140 may include a single server or a server group. The server group may be centralized or distributed. In some embodiments, the processing device 140 may be local to or remote from the medical system 100. For example, the processing device 140 may access information and/or data from the IGRT apparatus 110, the terminal 130, and/or the storage device 150 via the network 120. As another example, the processing device 140 may be directly connected to the IGRT apparatus 110, the terminal 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a computing device having one or more components as described in connection with FIG. 4.

In some embodiments, the processing device 140 may include one or more processors (e.g., single-core processor(s) or multi-core processor(s)). Merely by way of example, the processing device 140 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 150 may store data, instructions, and/or any other information. In some embodiments, the storage device 150 may store data obtained from one or more components of the medical system 100 (e.g., the IGRT apparatus 110, the terminal 130). In some embodiments, the storage device 150 may store data and/or instructions that the processing device 140 may execute or use to perform exemplary methods/systems described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the medical system 100 (e.g., the IGRT apparatus 110, the processing device 140, and/or the terminal device(s) 130). One or more components in the medical system 100 may access the data or instructions stored in the storage device 150 via the network 120. In some embodiments, the storage device 150 may be part of the processing device 140.

In some embodiments, the one or more components of the IGRT apparatus 110 (such as the treatment table 114, the scan source 115, the treatment head 116, the detector 112, and the EPID 113, etc.) may be moved based on control commands. The control commands may be determined based on treatment parameters (e.g., radiation dose) in a predetermined treatment plan and/or image information (e.g., an ROI image) or other information (e.g., feature information in the ROI image).

It should be noted that the above description of the medical system 100 is merely provided for the purposes of illustration, and not intended to limit the scope of the present disclosure. For persons having ordinary skills in the art, multiple variations and modifications may be made under the teachings of the present disclosure. For example, the assembly and/or function of the medical system 100 may be varied or changed according to specific implementation scenarios.

Figure 3:
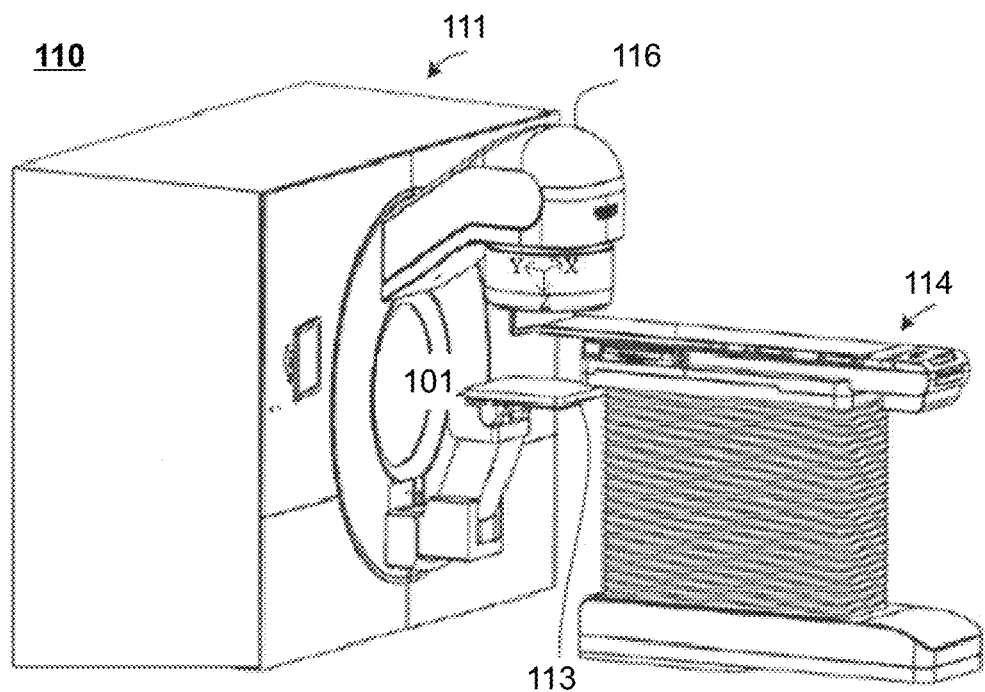
FIG. 3 is a schematic diagram illustrating an exemplary radiation therapy apparatus according to some embodiments of the present disclosure.

FIG. 3 is a schematic diagram illustrating an exemplary radiation therapy apparatus according to some embodiments of the present disclosure. The radiation therapy apparatus may be the IGRT apparatus 110 illustrated in FIG. 1. As illustrated in FIG. 3, the IGRT apparatus 110 may include a gantry 111, a treatment table 114, a treatment head 116, and an EPID 113. In some embodiments, an imaging component (not shown in FIG. 3) may be mounted on the gantry 111. The imaging component may include a CT device, a magnetic resonance imaging (MRI) device, or a positron emission tomography (PET) device, or the like, or any combination thereof.

In some embodiments, the gantry 111 may be a ring gantry with a substantially cylindrical configuration. The gantry 111 may be disposed on a base and be rotatable on the base. The gantry 111 may include a bore 101. The gantry 111 may rotate around a central axis of the bore 101. A rotation axis of the gantry 111 and the central axis of the bore 101 may be coaxial. The treatment head 116 and the EPID 113 may be respectively mounted on the gantry 111. In some embodiments, during the radiation therapy procedure, the treatment head 116 and the EPID 113 can be oppositely disposed on both sides of the rotation axis.

In some embodiments, the position of the treatment table 114 may be adjusted to obtain a guide image of a subject to be examined. The IGRT apparatus 110 may perform the radiation therapy for the subject based on information related to the guide image. For example, the treatment table 114 may be adjusted in a vertical direction in order to change a distance between the treatment table 114 and a horizontal plane (e.g., the floor). As another example, the treatment table 114 may move along the rotation axis of the gantry 111. The treatment table 114 may be moved into the bore 101 of the gantry 111, or may be moved out from the bore 101. As a further example, the treatment table 114 may be rotated on the horizontal plane.

In some embodiments, the treatment head 116 may include one or more beam limiting components (not shown in FIG. 3). For example, the one or more beam limiting components may include Y jaws, X jaws, the MLC, and so on. The one or more beam limiting components may be configured to control a shape and an irradiation area of the radiation beams by adjusting the structure of at least one beam limiting component.

In some embodiments, the EPID 113 may be a camera-based device, such as a flat plane imager with a detector array. The EPID 113 may include an array of solid state detectors (e.g., amorphous silicon-based detectors, or dosimeters), which may record the amount of radiation that impinge on them and convert the received amount of radiation into corresponding number (or count) of electrons. The electrons may be converted into electrical signals. A portal image may be generated based on the electrical signals. In some embodiments, for a treatment beam associated with a planned radiation dose and a planned gantry angle, the radiation beams can be irradiated onto the EPID 113, a sequence of portal images may be generated accordingly. The portal images may be converted to portal dose images (PDIs). The portal dose images may characterize dose distributions of radiation beams measured by the EPID 113.

Figure 4:
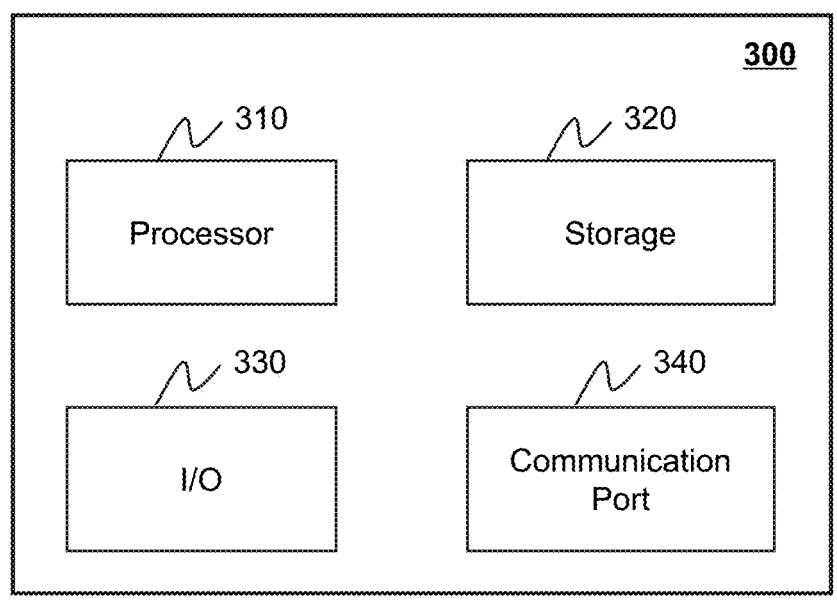
FIG. 4 is a schematic diagram illustrating hardware and/or software components of an exemplary computing device according to some embodiments of the present disclosure.

FIG. 4 is a schematic diagram illustrating hardware and/or software components of an exemplary computing device according to some embodiments of the present disclosure. In some embodiments, the processing device 140 illustrated in FIG. 1 or FIG. 2 may be implemented on computing device 300 illustrated in FIG. 4. As illustrated in FIG. 4, the computing device 300 may include a processor 310, a storage 320, an input/output (I/O) 330, and a communication port 340.

The processor 310 may execute computer instructions (program codes) and perform functions of the processing device 140 in accordance with techniques described herein. The computer instructions may include, for example, routines, programs, objects, components, signals, data structures, procedures, modules, and functions, which perform particular functions described herein. For example, the processor 310 may process image data obtained from the IGRT apparatus 110, the terminals(s) 130, the storage device 150, and/or any other component of the medical system 100. In some embodiments, the processor 310 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the IGRT apparatus 110, the terminal(s) 130, the storage device 150, and/or any other component of the medical system 100. In some embodiments, the storage 320 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store programs or codes that the processing device 140 processes image data related to a subject.

The input/output (I/O) 330 may input or output signals, data, and/or information. In some embodiments, the I/O 330 may enable user interaction with the processing device 140. In some embodiments, the I/O 330 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected with a network (e.g., the network 120) to facilitate data communications. The communication port 340 may establish connections between the processing device 140 and the IGRT apparatus 110, the terminal 130, and/or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, 6G, etc.), or the like, or any combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 5:
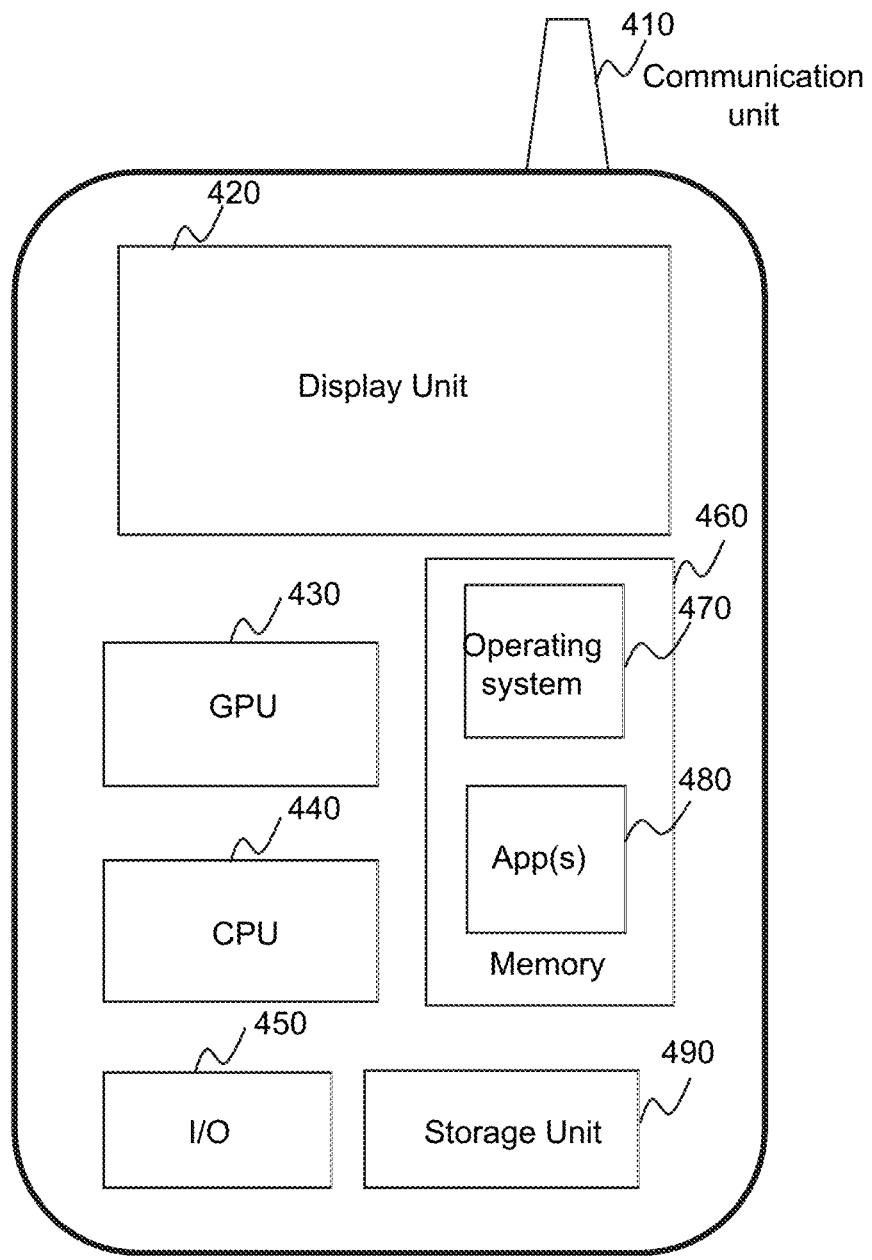
FIG. 5 is a schematic diagram illustrating hardware and/or software components of an exemplary mobile device according to some embodiments of the present disclosure.

FIG. 5 is a schematic diagram illustrating hardware and/or software components of an exemplary mobile device according to some embodiments of the present disclosure. In some embodiments, the terminal 130 may be implemented on the mobile device 131 illustrated in FIG. 5. As illustrated in FIG. 5, the mobile device 131 may include a communication unit (e.g., an antenna) 410, a display unit 420, a graphics processing unit (GPU) 430, a central processing unit (CPU) 440, an I/O 450, a memory 460, and a storage unit 490. In some embodiments, any other suitable component, including but not limited to a system bus or a controller (not shown), may also be included in the mobile device 131. In some embodiments, a mobile operating system 470 (e.g., iOS, Android, Windows Phone, Harmony OS, etc.) and one or more applications 480 may be loaded into the memory 460 from the storage unit 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the medical system 100 via the network 120.

To implement various modules, units, and functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 6:
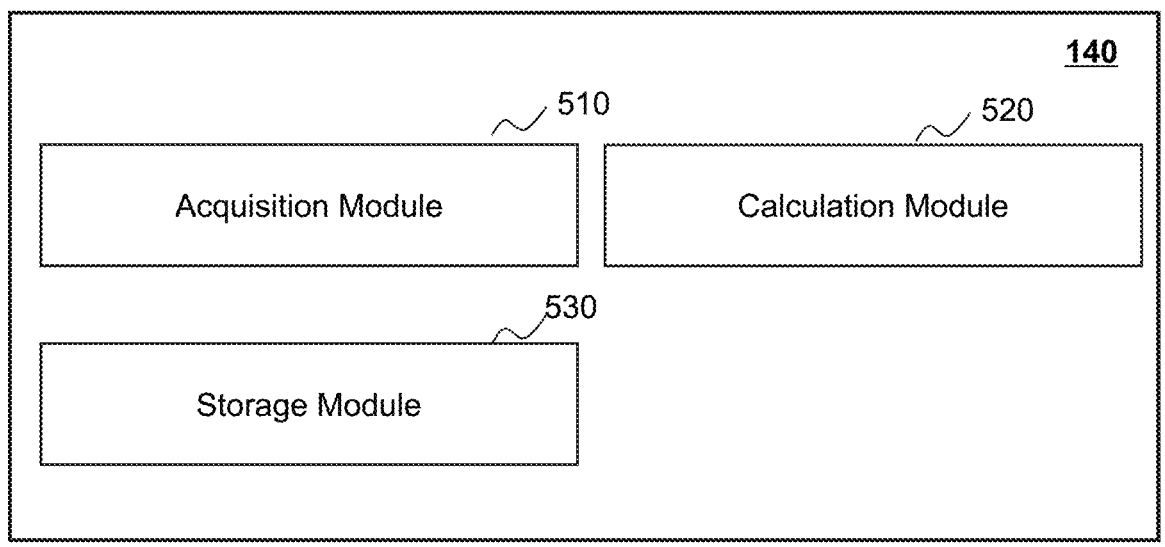
FIG. 6 is a block diagram illustrating an exemplary processing device according to some embodiments of the present disclosure.

FIG. 6 is a block diagram illustrating an exemplary processing device according to some embodiments of the present disclosure. In some embodiments, the processing device 140 may be implemented on the computing device 300 (e.g., the processor 310) illustrated in FIG. 4 or a CPU 440 as illustrated in FIG. 5. As shown in FIG. 6, the processing device 140 may include an acquisition module 510, a calculation module 520, and a storage module 530. Each of the modules described above may be a hardware circuit that is designed to perform certain actions, e.g., according to a set of instructions stored in one or more storage media, and/or any combination of the hardware circuit and the one or more storage media.

The acquisition module 510 may be configured to obtain information from one or more components (e.g., the IGRT apparatus 110, the one or more terminals 130, the storage device 150, etc.) of the medical system 100. For example, the acquisition module 510 may obtain a plurality of raw images with respect to measured radiation beams through the EPID 113. As another example, the acquisition module 510 may acquire obtain one or more calibration parameters from a storage device (e.g., the storage device 150 or the storage module 530). The one or more calibration parameters may include a position offset value, a detector gain value and/or a curve correction value. As a further example, the acquisition module 510 may obtain a predetermined treatment plan from a treatment plan system (TPS). In accordance with the predetermined treatment plan, at a planned gantry angle, radiation beams with a planned radiation dose may be delivered. In some embodiments, the acquisition module 510 may send the acquired data to the calculation module 520, and/or the storage module 530.

The calculation module 520 may be configured to determine differences between a planned radiation dose distribution and an actual radiation dose distribution (i.e., the actual dose delivered to the target during the radiation treatment). In some embodiments, the calculation module 520 may determine a measured dose image. The calculation module 520 may determine an energy fluence distribution map related to radiation beams predicted by a first portal dose prediction model. The first portal dose prediction model may simulate or predict the radiation beams corresponding to the planned radiation dose and the planned gantry angle. In some embodiments, the first portal dose prediction model may include a Monte Carlo (MC) simulation model. The calculation module 520 may determine a predicted dose image based on the energy fluence distribution map and a simulated energy response curve related to the EPID 113. In some embodiments, the simulated energy response curve related to the EPID 113 may be determined in advance by modeling an energy deposition efficiency of the EPID 113. The calculation module 520 may determine differences between the measured and predicted dose images by comparing dose distributions of the measured and predicted dose images. For example, the calculation module 520 may quantitatively estimate the differences between the measured and predicted dose images based on a gamma evaluation method. More descriptions regarding the comparison of the measured dose image and the predicted dose image may be found elsewhere in the present disclosure (e.g., FIG. 7 and the descriptions thereof).

The storage module 530 may be configured to store data and/or information from the medical system 100. For example, the storage module 530 may store the one or more calibration parameters. The storage module 530 may store an output correction factor. The storage module 530 may store an absolute dose correction factor. It should be noted that any data or information generated during the pre-treatment QA verification and the radiation treatment may be stored in the storage module 530.

It should be noted that the above description of the processing device 140 is provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the storage module 530 may be omitted. As another example, the calculation module 520 may be omitted, while the IGRT apparatus 110 and/or the one or more terminals 130 may be configured to perform one or more functions of the calculation module 520 described in the present disclosure.

Figure 7:
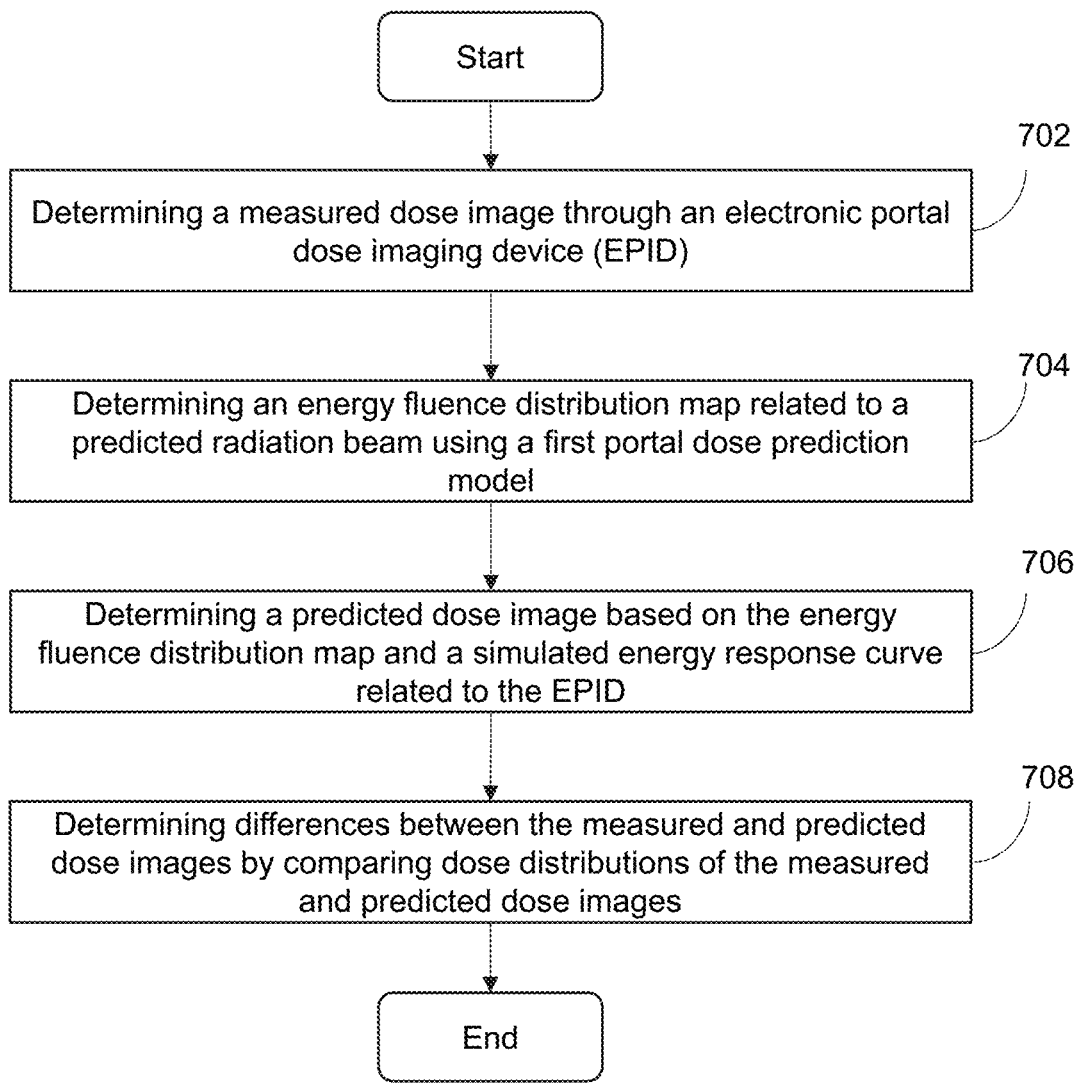
FIG. 7 is a flowchart illustrating an exemplary process for verifying radiation dose according to some embodiments of the present disclosure.

FIG. 7 is a flowchart illustrating an exemplary process for verifying radiation dose according to some embodiments of the present disclosure. In some embodiments, the process 700 illustrated in FIG. 7 may be adopted for pre-treatment quality assurance (QA) in a radiation treatment. In some embodiments, the process 700 may be executed by the medical system 100. For example, the process 700 may be implemented as a set of instructions (e.g., an application) stored in a storage device (e.g., the storage device 150, the storage 320, and/or the storage unit 490). In some embodiments, the processing device 140 (e.g., the processor 310 of the computing device 300, the CPU 440 of the mobile device 131, and/or one or more modules illustrated in FIG. 6) may execute the set of instructions to perform the process 700. The operations of the illustrated process presented below are intended to be illustrative. In some embodiments, the process 700 may be accomplished with one or more additional operations not described and/or without one or more of the operations discussed. Additionally, the order of the operations of the process 700 illustrated in FIG. 7 and described below is not intended to be limiting.

In 702, the processing device (e.g., the calculation module 520 of the processing device 140) may determine a measured dose image through an electronic portal imaging device (EPID). The measured dose image refers to a portal dose image measured by the EPID (e.g., the EPID 113) and indicates a dose distribution of radiation beams measured by the EPID.

In some embodiments, a predetermined treatment plan may be obtained from a treatment plan system (TPS) of the medical system 100. The predetermined treatment plan may include a radiation dose, a radiation rate, a dose rate, a radiation time, or the like, or any combination thereof. In some embodiments, in accordance with the predetermined treatment plan, a treatment head of an IGRT apparatus (e.g., the treatment head 116 of the IGRT apparatus 110) may emit and deliver radiation beams with a planned radiation dose and at a specific gantry angle. In some embodiments, the planned radiation dose can need to be verified prior to the first treatment of the subject (e.g., the patient). The actual radiation delivery may be made based on the planned radiation dose.

Merely by way of example, for the pre-treatment portal dosimetry verification, in accordance with the predetermined treatment plan, the treatment head 116 may be positioned at a planned gantry angle and deliver the radiation beams with a planned radiation dose towards the EPID 113. There is no attenuating medium between the treatment head 116 and the EPID 113 during the radiation delivery. For example, during the radiation delivery, the subject and/or the treatment table may not be placed between the treatment head 116 and the EPID 113. The radiation beams can impinge directly on the plane of the EPID 113. The EPID 113 may acquire a plurality of raw images in response to electrical signals resulting from the incident radiation beams. The plurality of raw images may be a sequence of image frames. Each image frame may be a portal image. In some embodiments, a pixel (or voxel) value of the portal image may correspond to a dose value of a portal dose image. The portal dose image may be indicative of a dose distribution of the radiation beams impinging on the EPID 113. In some embodiments, the measured raw images may be converted to the measured dose image.

In some embodiments, the measured raw image (e.g., the measured portal images) may be calibrated based one or more calibration parameters. The one or more calibration parameters may include a position offset value, a detector gain value and/or a curve correction value. In some embodiments, the one or more calibration parameters may be predetermined, for example, with reference to the descriptions of FIG. 9. In some embodiments, each measured raw image may be calibrated based on the one or more calibration parameters. The calibrated raw images may be summarized to form a final calibrated image. The final calibrated image may be converted to the measured dose image. In some embodiments, the measured raw images may be summarized. The summarized image may be calibrated based on the one or more calibration parameters, thereby forming a final calibrated image. The final calibrated image may be converted to the measured dose image. More descriptions regarding the determination of the measured dose image may be found elsewhere in the present disclosure (e.g., FIGS. 8A and 8B, and the descriptions thereof).

In 704, the processing device (e.g., the calculation module 520 of the processing device 140) may determine an energy fluence distribution map related to radiation beams predicted by a first portal dose prediction model.

In some embodiments, the first portal dose prediction model may simulate the radiation delivery procedure (e.g., particle transport) between the treatment head 116 and the EPID 113. For example, the first portal dose prediction model may simulate or predict the radiation beams corresponding to the planned radiation dose and the planned gantry angle.

In some embodiments, the first portal dose prediction model may include a Monte Carlo (MC) simulation model. The MC simulation method, also called a random sampling technique, is a computational technique that is fundamentally different from a general numerical calculation technique, and belongs to a branch of experimental mathematics. The MC simulation can use random numbers for a statistical test and obtain statistical feature values (such as a mean, a probability, etc.) as numerical solutions to the problem to be solved. In the TPS for predetermining the treatment plan, an MC dose calculation algorithm may be applied to sample particles (e.g., photons or electrons) and transport the particles, determine an energy deposition when the particles interact with a reaction cross-section of different materials, generate secondary particles for coupled MC transport, and determine a dose of an point of interest (POI) or a dose distribution of an interest of region.

In some embodiments, the MC simulation model may be a geometric model of the whole LINAC head (e.g., the treatment head 116). In the MC simulation model, all components (e.g., the target, the primary collimator, the flattening filter, the jaws, and the MLC) of the treatment head 116 may be modeled (e.g., via a MC simulation software (e.g., DOSXYZ)). In some embodiments, the MC simulation model may further include a plane below the collimating system (e.g., the MLC). The plane is called a phase-space plane. A phase-space file of the phase-space plane may be obtained. The phase-space file may contain file parameters, such as position, direction, energy or charge of all particles hitting the phase-space plane. In some embodiments, the plane (and the file) may be used as a source for the MC transport simulation. The energy fluence distribution map may be generated based on the file parameters of the phase-space file.

In some embodiments, a virtual source model may be constructed based on the MC simulation technique. The virtual source model is one type of the MC simulation model. In some embodiments, the virtual source model may be deemed as a parameterization of the phase-space file including several sub-sources (e.g., the target, the primary collimator, the flattening filter, the charged particles, etc.) and serve as a particle generator for the MC simulation. The virtual source model may generate particle distributions indicative of the energy fluence distribution map using the MC dose calculation algorithm. In some embodiments, during the simulation of the virtual source model, a plurality of parameters (e.g., a radius of a primary source or a secondary source, an energy spectrum, an off-axis softening coefficient, etc.) of the virtual source model may be adjusted such that the calculated contours of different square fields and the percent depth dose (PDD) curves can be consistent with corresponding measured data. In this case, the particle distribution calculated or predicted by the virtual source model may be consistent with the particle distribution in a radiation beam emitted from the treatment head 116. The energy fluence distribution map of the predicted particle distribution may be determined. It is understood that the energy fluence distribution map is a calculated result of the MC simulation model, and it is not an actual measured result.

In some embodiments, the energy fluence distribution map may characterize the particle distribution on the plane of the EPID 113, but not the particles' entry into or reaction with the EPID 113. In some embodiments, the MC simulation model may also be used to simulate the process of the particles entering and reacting with EPID 113, but the simulation process is time-consuming. Thereby, the simulation process of the particles entering and reacting with EPID 113 may be omitted in the determination of the energy fluence distribution map, which may improve the computational efficiency in the MC simulation.

In 706, the processing device (e.g., the calculation module 520 of the processing device 140) may determine a predicted dose image based on the energy fluence distribution map and a simulated energy response curve related to the EPID (e.g., the EPID 113). The predicted dose image may be indicative of a dose distribution of the predicted radiation beams generated by the first portal dose prediction model.

In some embodiments, the simulated energy response curve related to the EPID 113 may be determined in advance by modeling an energy deposition efficiency of the EPID 113. The transport of the particles in the EPID 113 may be simulated. A Monte Carlo (MC) dose engine (or the MC simulation software) may be applied to simulate the transport of the particles in the EPID 113. Exemplary MC dose engines may include DOSXYZ, EGS4/EGSnrc, MCNP, GEANT4, or the like. As used herein, DOSXYZ (an open source MC simulation software) may be selected as the MC dose engine. The MC dose engine may model the detector structure of the EPID 113 and obtain the energy deposition efficiency of different-energy particles entering the EPID 113. The EPID 113 may include an array of solid-state detectors (e.g., amorphous silicon-based detectors, or dosimeters). For example, the size of the detector array may be 1024×1024. The detector array of the EPID 113 may be modeled through the DOSXYZ. Then the energy deposition efficiency of particles of different incident energies may be determined based on the modeled detector array.

Figure 11:
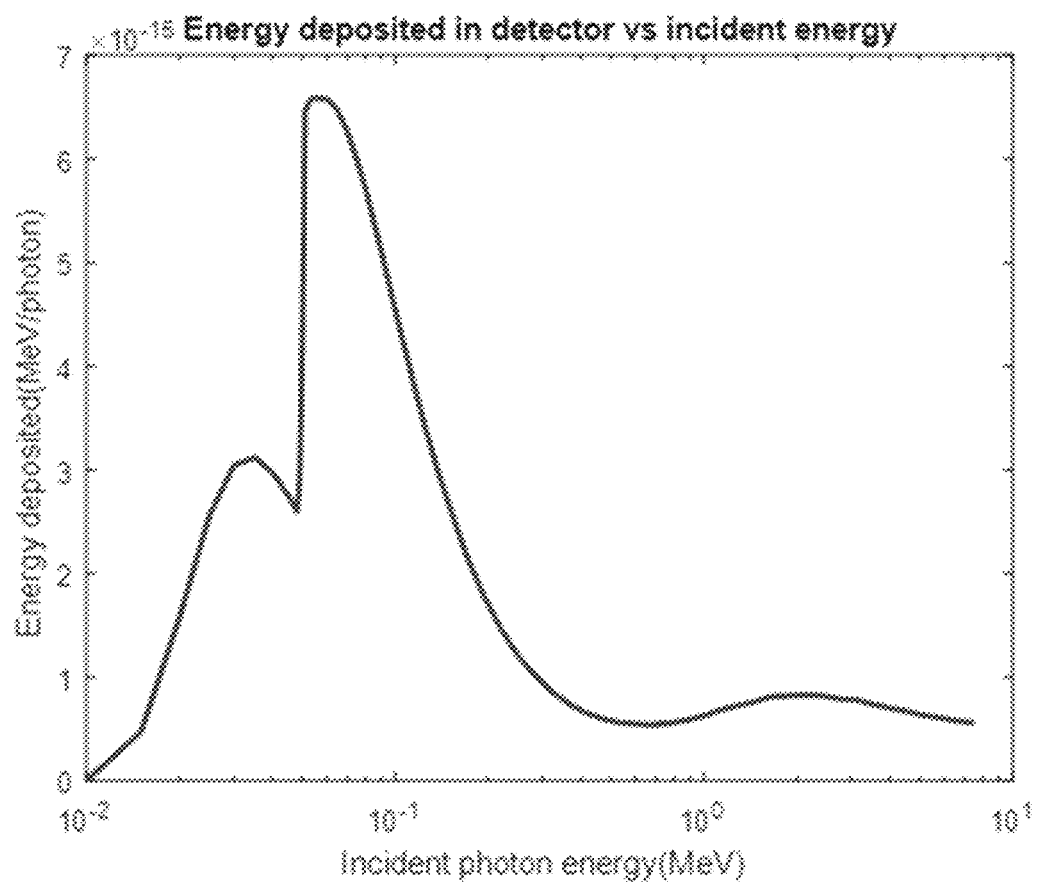
FIG. 11 illustrates a simulated energy response curve related to an EPID according to some embodiments of the present disclosure.

FIG. 11 illustrates a simulated energy response curve related to the EPID (e.g., the EPID 113) according to some embodiments of the present disclosure. The simulated energy response curve may characterize that the energy deposited in detector varying with incident energy of the particles. As illustrated in FIG. 11, the horizontal axis represents an incident photon energy (Mev) and the vertical axis represents an energy deposition efficiency (Mev/photon). In some embodiments, the relevant data of the energy response curve (e.g., incident energies and/or deposited energies in the detectors) may be stored in the form of a data table or figure. In some embodiments, the data table may be stored in a storage device (e.g., the storage device 150 or the storage module 530). In some embodiments, the energy deposition efficiency of different incident particles may be obtained by looking up the stored data table or figure. By the way of looking up the data table or figure of the energy response curve, the simulation of complex particle transport using the MC dose algorithm may be avoided, and the computational speed and/or the accuracy of the MC dose engine may be improved.

In some embodiments, the predicted dose image may be calculated based on the calculated energy fluence distribution map and the simulated energy response curve. For example, the calculation module 520 may multiply the energy fluence distribution map by the simulated energy response curve to form the predicted dose image. The predicted dose image may characterize the dose distribution of the predicted radiation beams generated by the first portal dose prediction model.

In 708, the processing device (e.g., the calculation module 520 of the processing device 140) may determine differences between the measured and predicted dose images by comparing dose distributions of the measured and predicted dose images. As mentioned above, the measured dose image may be indicative of the dose distribution of the radiation beams measured by the EPID 113. The predicted dose image may be indicative of the dose distribution of the radiation beams predicted (or calculated) by the first portal dose prediction model (e.g., the MC simulation model). The measured radiation beams and the predicted radiation beams may be associated with the planned radiation dose. In some embodiments, the differences between the measured dose distribution and the predicted dose distribution are an indication of radiation dose delivery errors. According to the comparison of the measured dose distribution and the predicted dose distribution, the processing device may determine whether the planned radiation dose is reasonable.

In some embodiments, the processing device 140 may quantitatively estimate the differences between the measured and predicted dose images based on a gamma evaluation technique. The gamma evaluation technique may combine a dose difference criterion with a distance-to-agreement (DTA) criterion. In some embodiments, the DTA is the distance between a measured data point (e.g., a pixel in the measured dose image) and the nearest data point (e.g., a pixel in the predicted dose image) in the predicted dose distribution that exhibits the same radiation dose. In some embodiments, a relative dose difference between the measured dose image and the predicted dose image may be calculated by comparing a first data point in the measured dose distribution with a second data point in the predicted dose distribution.

Merely by way of example, a general representation of the gamma evaluation method for determining an acceptance criterion that considers both the dose difference and the DTA is as follows:

$$\Gamma(r_p, r_m) = \sqrt{\frac{r^2(r_p, r_m)}{\Delta d^2} + \frac{\delta^2(r_p, r_m)}{\Delta D^2}}, \quad (1)$$

whereas $r(r_p, r_m) = \sqrt{\Delta x_{p-m}^2 + \Delta y_{p-m}^2}$, (2)

and $\delta(r_p, r_m) = D_p(r_p) - D_m(r_m)$, (3)

where $\Gamma$ represents a gamma value; r represents a spatial distance between a predicted data point (pixel or voxel) $r_p$ in the predicted dose distribution and a measured data point $r_m$ in the measured dose distribution; $x_p$ and $x_m$ represent the locations along the X axis of the predicted and measured data points (i.e., $r_p$ and $r_m$), respectively; $y_p$ and $y_m$ represent the locations along the Y axis of the predicted and measured data points (i.e., $r_p$ and $r_m$), respectively; $\Delta x_{p-m}$ represents the location difference between $x_p$ and $x_m$; $\Delta y_{p-m}$ represents the location difference between $y_p$ and $y_m$; $\delta$ represents a dose difference between the predicted and measured data points; $D_p$ represents the predicted dose value of the predicted data point $r_p$, and $D_m$ represents the measured dose value of the measured point $r_m$; $\Delta D$ represents a dose difference criteria and $\Delta d$ represents a DTA criteria, for example, $\Delta D=3\%$ and $\Delta d=3$ mm.

In some embodiments, a gamma index belonging to a predicted data point $r_p$ may be determined based on $\gamma$ function as follows:

$$\gamma(r_p) = \min\{\Gamma(r_p, r_m)\} \forall \{r_m\}. \quad (4)$$

According to the $\gamma$ function, a minimum generalized gamma value $\Gamma$ may be chosen among *** as the gamma index for the predicted data point $r_p$. In some embodiments, a statistical gamma pass rate may be determined based on a pass-fail criterion. The pass-fail criteria may be defined as follows:

$$\begin{cases} \gamma(r_p) \leq 1, \text{ calculation passes} \\ \gamma(r_p) > 1, \text{ calculation fails} \end{cases} \quad (5)$$

When the gamma index is greater than 1, the dose calculation may be considered as "fail." When the gamma index is less than or equal to 1, the dose calculation may be considered as "pass." The gamma pass rate may be calculated based on a ratio of the number of the passed data points to all measured data points. It should be noted that, in some embodiments, when the gamma index is equal to 1, the dose calculation may be considered as "fail."

In some embodiments, the processing device 140 may select a plurality of specific measured points in the measured dose image. For example, the plurality of specific measured points may include all data points in the measured dose image. As another example, the plurality of specific measured points may include a portion of the data points in the measured dose image, such as 50×50 pixels. The processing device may determine the gamma pass rate based on the ratio of the number (or count) of the passed data points to the number (or count) of all the measured data points. For example, given that the number (or count) of the specific measured points is 2,500 and the number (or count) of the passed data points is 2,400, the gamma pass rate is 96% (i.e., 2400/2500). In some embodiments, if the gamma pass rate exceeds a threshold value (e.g., 98%), the dose differences between the measured dose image and the predicted dose image may be deemed negligible, that is, the radiation delivery errors may be neglected. The predetermined treatment plan may be considered as reasonable. If the gamma pass rate is below the threshold value, the dose differences between the measured dose image and the predicted dose image may be considered exceeding the acceptance criterion of the radiation delivery errors. The predetermined treatment plan may be considered as unreasonable, which may result in an inaccurate radiation therapy. The predetermined treatment plan may need to be adjusted in order to eliminate or reduce the radiation dose delivery errors.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in some embodiments, the determinations of the measured dose image and the predicted dose image may be performed simultaneously, such as operation 702 being performed simultaneously with operations 704-706.

Figure 8A:
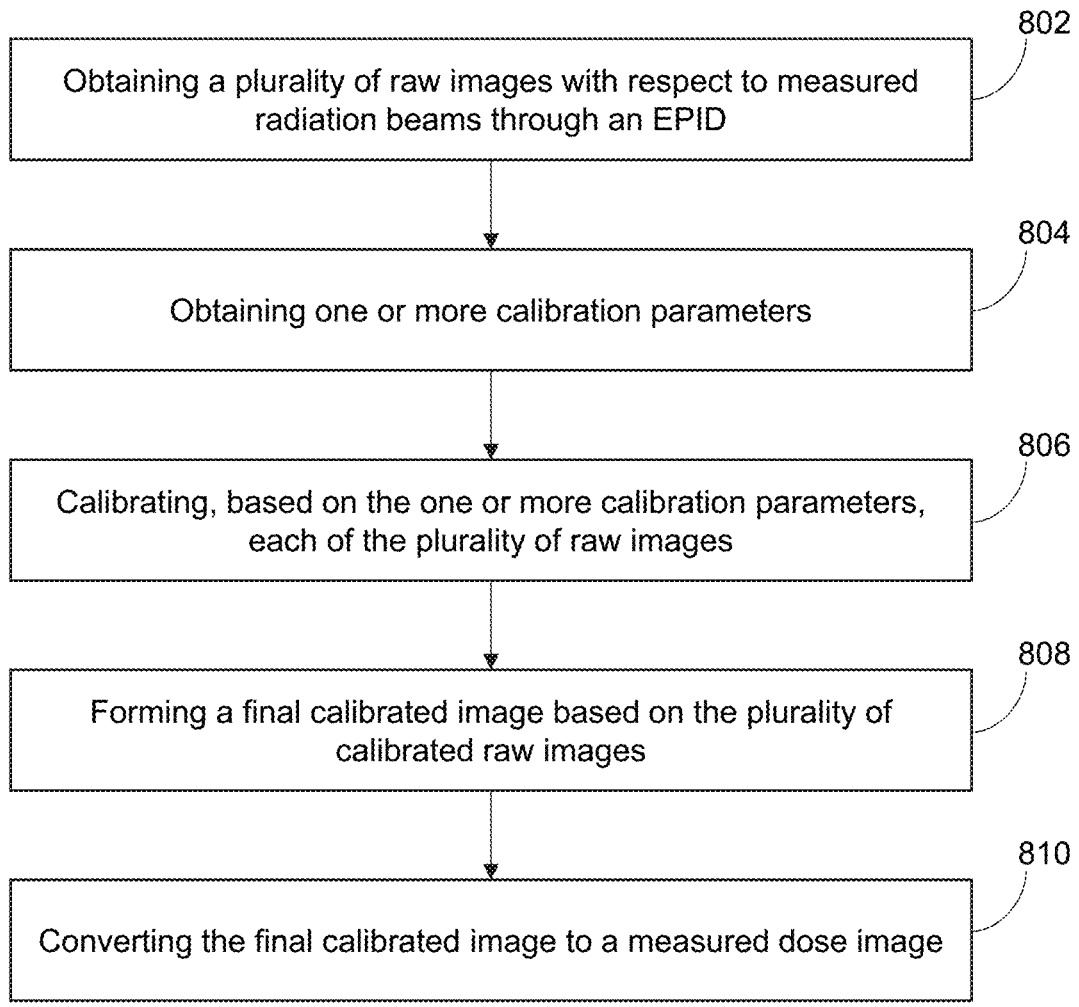
FIG. 8A is a flowchart illustrating an exemplary process for determining a measured dose image according to some embodiments of the present disclosure.
Figure 8B:
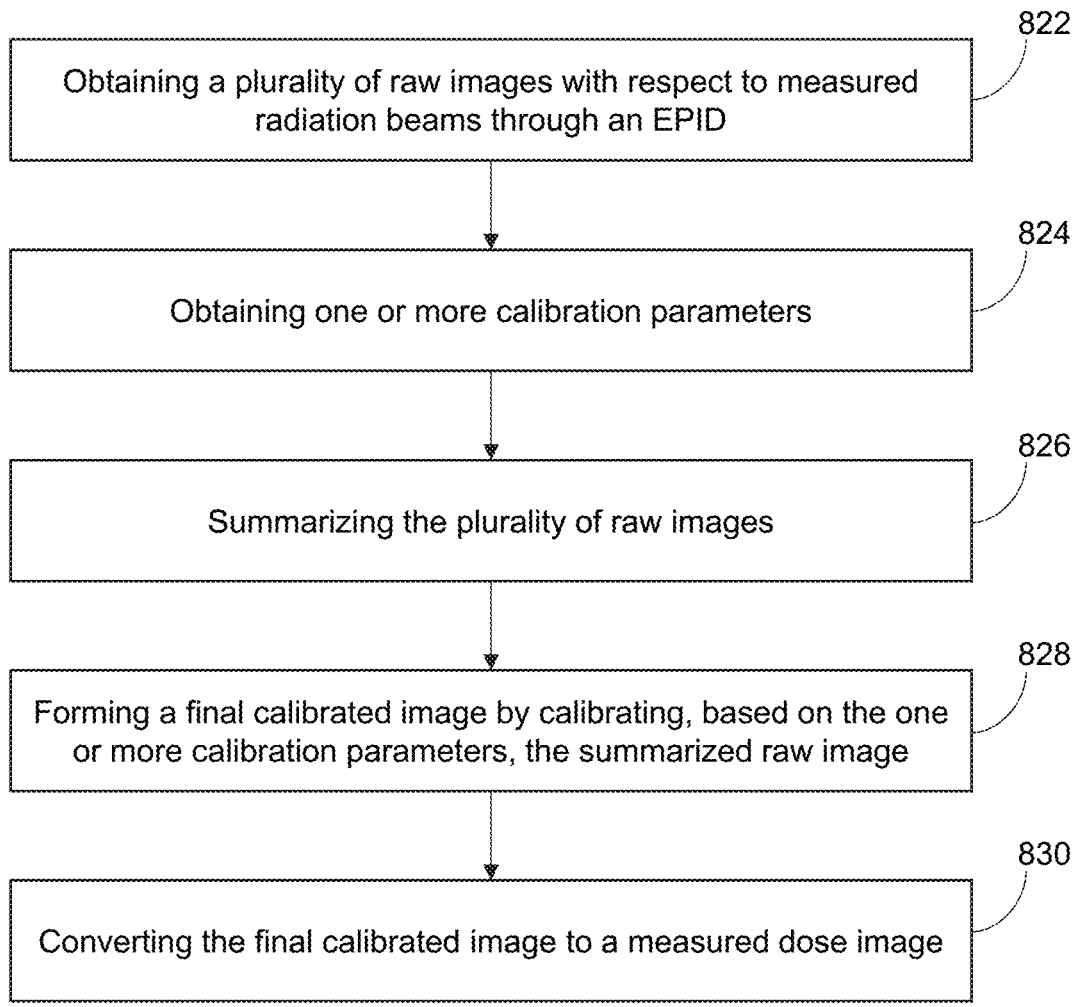
FIG. 8B is a flowchart illustrating an exemplary process for determining a measured dose image according to some embodiments of the present disclosure.

FIGS. 8A and 8B illustrate exemplary processes for determining a measured dose image according to some embodiments of the present disclosure. The determined measured dose image may be indicative of a dose distribution of radiation beams measured by an EPID (e.g., the EPID 113). In some embodiments, the process illustrated in FIG. 8A or 8B may be executed by the medical system 100. For example, the process illustrated in FIG. 8A or 8B may be implemented as a set of instructions (e.g., an application) stored in a storage device (e.g., the storage device 150, the storage 320, and/or the storage unit 490). In some embodiments, the processing device 140 (e.g., the processor 310 of the computing device 300, the CPU 440 of the mobile device 131, and/or one or more modules illustrated in FIG. 6) may execute the set of instructions to perform the process illustrated in FIG. 8A or 8B. The operations of the illustrated process presented below are intended to be illustrative. In some embodiments, the process illustrated in FIG. 8A or 8B may be accomplished with one or more additional operations not described and/or without one or more of the operations discussed. Additionally, the order of the operations of the process illustrated in FIG. 8A or 8B and described below is not intended to be limiting.

FIG. 8A is a flowchart illustrating an exemplary process for determining a measured dose image according to some embodiments of the present disclosure.

In 802, the processing device (e.g., the acquisition module 510 of the processing device 140) may obtain a plurality of raw images with respect to measured radiation beams through an EPID (e.g., the EPID 113). As used herein, the measured radiation beams refer to radiation beams detected or measured by the EPID 113.

As described in connection with operation 702 illustrated in FIG. 7, in accordance with the predetermined treatment plan, the treatment head 116 may be positioned at a planned gantry angle and deliver the radiation beams with a planned radiation dose towards the EPID 113. There is no attenuating medium between the treatment head 116 and the EPID 113 during the radiation delivery. For example, during the radiation delivery, the subject and/or the treatment table may not be placed between the treatment head 116 and the EPID 113. The radiation beams can impinge directly on the plane of the EPID 113. The EPID 113 may acquire the plurality of raw images in response to electrical signals resulting from the incident radiation beams. The plurality of raw images may be a sequence of image frames. Each image frame may be a portal image.

In 804, the processing device (e.g., the acquisition module 510 of the processing device 140) may obtain one or more calibration parameters. The one or more calibration parameters may include a position offset value, a detector gain value, and/or a curve correction value. In some embodiments, the one or more calibration parameters may be predetermined, for example, with reference to the descriptions of FIG. 9.

In 806, the processing device (e.g., the calculation module 520 of the processing device 140) may calibrate, based on the one or more calibration parameters, each of the plurality of raw images.

In some cases, the centers of the portal image and the EPID may misalign due to some unavoidable errors (e.g., assembly errors of the EPID 113). In some embodiments, the processing device may align the centers of the portal image and the EPID 113 based on the position offset value. For illustrative purposes, the position offset value can be represented by $(\Delta x, \Delta y)$, where $\Delta x$ and $\Delta y$ represent a position deviation of X-coordinate and Y-coordinate of the portal image and the EPID 113, respectively. The coordinates of a pixel in the portal image can be represented by $(x, y)$, where $x$ and $y$ represent X-coordinate and Y-coordinate of the portal image, respectively. To align the centers of the portal image and the EPID 113, the processing device 140 may calibrate the coordinates of each pixel of the portal image based on the position offset value. The coordinates of each pixel of the calibrated portal image can be expressed as $(x+\Delta x, y+\Delta y)$. It is understood that, through the position calibration for each portal image, respective centers of the plurality of portal images may be aligned with the center of the EPID 113. As used herein, the calibrated portal image through the position offset may be designated as a first calibrated image.

In some embodiments, to eliminate or reduce the sensitivity difference of the detectors of the EPID 113 for the particles of different energies, the processing device may process the first calibrated image using the detector gain value. In some embodiments, the detector gain value may be in the form of a matrix, that is, the detector gain matrix. The dimensions of the detector gain matrix and the first calibrated image may be equal, such as 1024×1024. In some embodiments, the processing device may divide the first calibrated image by the detector gain matrix to form a second calibrated image.

In some embodiments, to eliminate the over-response of the detectors of the EPID 113 for the particles of low energy, the processing device may process the second calibrated image using the curve correction value. In some embodiments, the curve correction value may be in the form of a matrix as well, that is, the curve correction matrix. The dimensions of the curve correction matrix and the second calibrated image may be equal, such as 1024×1024. In some embodiments, the processing device may multiply the second calibrated image by the curve correction matrix to form a third calibrated image. More descriptions regarding the determination of the one or more calibration parameters may be found elsewhere in the present disclosure (e.g., FIG. 9 and the descriptions thereof).

In 808, the processing device (e.g., the calculation module 520 of the processing device 140) may form a final calibrated image based on the plurality of calibrated raw images. As described above, each raw image (e.g., each portal image) may be calibrated to form a corresponding third calibrated image based on the position offset value, the detector gain matrix and the curve correction matrix. In some embodiments, the plurality of third calibrated images may be summarized to from the final calibrated image. In the final calibrated image, a pixel value may be equal to a sum of the values of pixels at the same pixel location in each third calibrated image.

In 810, the processing device (e.g., the calculation module 520 of the processing device 140) may convert the final calibrated image to a measured dose image. The measured dose image may be a portal dose image (PDI) indicative of the dose distribution at the plane of the EPID 113. In some embodiments, the processing device may convert the final calibrated image to the portal dose image using a portal dose reconstruction algorithm (e.g., Monte Carlo dose calculation algorithm). For example, grey-scale pixel values of the final calibrated image may be converted to dose values of the measured dose image.

FIG. 8B is a flowchart illustrating an exemplary process for determining a measured dose image according to some embodiments of the present disclosure.

In 822, the processing device (e.g., the acquisition module 510 of the processing device 140) may obtain a plurality of raw images with respect to measured radiation beams through an EPID (e.g., the EPID 113). As used herein, the measured radiation beams refer to radiation beams detected or measured by the EPID 113.

As described in connection with operation 702 illustrated in FIG. 7, in accordance with the predetermined treatment plan, the treatment head 116 may be positioned at a planned gantry angle and deliver the radiation beams with a planned radiation dose towards the EPID 113. There is no attenuating medium between the treatment head 116 and the EPID 113 during the radiation delivery. For example, during the radiation delivery, the subject and/or the treatment table may not be placed between the treatment head 116 and the EPID 113. The radiation beams can be impinge directly on the plane of the EPID 113. The EPID 113 may acquire the plurality of raw images in response to electrical signals resulting from the incident radiation beams. The plurality of raw images may be a sequence of image frames. Each image frame may be a portal image.

In 824, the processing device (e.g., the acquisition module 510 of the processing device 140) may obtain one or more calibration parameters. The one or more calibration parameters may include a position offset value, a detector gain value and/or a curve correction value. In some embodiments, the one or more calibration parameters may be predetermined, for example, with reference to the descriptions of FIG. 9.

In 826, the processing device (e.g., the calculation module 520 of the processing device 140) may summarize the plurality of raw images (e.g., the portal images). For example, for each portal image, the values of pixels at the same pixel location may be summed. In the summarized raw image (SRI), a pixel value may be equal to a sum of the values of pixels at the same pixel location in each portal image.

In 828, the processing device (e.g., the calculation module 520 of the processing device 140) may form a final calibrated image by calibrating, based on the one or more calibration parameters, the summarized raw image (e.g., the sum of the raw images).

In some embodiments, the processing device may align the centers of the SRI and the EPID 113 based on the position offset value. For illustrative purposes, the position offset value can be represented by ($\Delta x$, $\Delta y$), where $\Delta x$ and $\Delta y$ represent a position deviation of X-coordinate and Y-coordinate of the SRI and the EPID 113, respectively. The coordinates of a pixel in the SRI can be represented by (x, y), where x and y represent X-coordinate and Y-coordinate of the SRI, respectively. To align the centers of SRI and the EPID 113, the processing device 140 may calibrate the coordinates of each pixel of the SRI based on the position offset value. The coordinates of each pixel of the calibrated SRI can be expressed as (x+$\Delta x$, y+$\Delta y$). It is understood that, through the position calibration for the SRI, the centers of the calibrated EPI and the EPID 113 may be aligned. As used herein, the calibrated SRI may be designated a fourth calibrated image.

In some embodiments, to eliminate the sensitivity difference of the detectors of the EPID 113 for the particles of different energies, the processing device may process the fourth calibrated image using the detector gain value. In some embodiments, the detector gain value may be in the form of a matrix, that is, the detector gain matrix. The dimensions of the detector gain matrix and the fourth calibrated image may be equal, such as 1024×1024. In some embodiments, the processing device may divide the fourth calibrated image by the detector gain matrix to form a fifth calibrated image.

In some embodiments, to eliminate the over-response of the detectors of the EPID 113 for the particles of low energy, the processing device may process the fifth calibrated image using the curve correction value. In some embodiments, the curve correction value may be in the form of a matrix as well, that is, curve correction matrix. The dimensions of the curve correction matrix and the second calibrated image may be equal, such as 1024×1024. In some embodiments, the processing device may multiply the fifth calibrated image by the curve correction matrix to form the final calibrated image. More descriptions regarding the determination of the one or more calibration parameters may be found elsewhere in the present disclosure (e.g., FIG. 9 and the descriptions thereof).

In 830, the processing device (e.g., the calculation module 520 of the processing device 140) may convert the final calibrated image to a measured dose image. The measured dose image may be a portal dose image (PDI) indicative of the dose distribution at the plane of the EPID 113. In some embodiments, the processing device may convert the final calibrated image to the portal dose image using a portal dose reconstruction algorithm (e.g., Monte Carlo dose calculation algorithm). For example, grey-scale pixel values of the final calibrated image may be converted to dose values of the measured dose image.

It should be noted that the above description of FIG. 8A or FIG. 8B is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in FIG. 8A or 8B, operations 802-804 or operations 822-824 may be integrated into a single operation.

Figure 9:
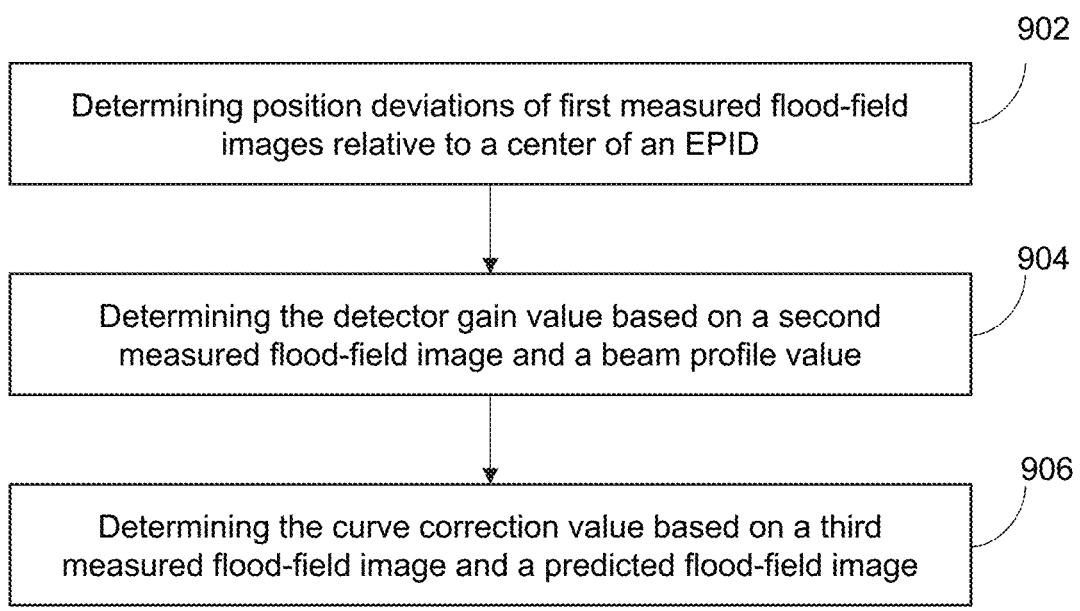
FIG. 9 is a flowchart illustrating an exemplary process for determining calibration parameters according to some embodiments of the present disclosure.

FIG. 9 is a flowchart illustrating an exemplary process for determining calibration parameters according to some embodiments of the present disclosure. In some embodiments, the calibration parameters may include a position offset value, a detector gain value and a curve correction value described in FIG. 7, and FIGS. 8A-8B. The calibrated parameters may be used to calibrate a plurality of raw images (e.g., portal images) generated by the EPID 113. In some embodiments, the process illustrated in FIG. 9 may be executed by the medical system 100. For example, the process illustrated in FIG. 9 may be implemented as a set of instructions (e.g., an application) stored in a storage device (e.g., the storage device 150, the storage 320, and/or the storage unit 490). In some embodiments, the processing device 140 (e.g., the processor 310 of the computing device 300, the CPU 440 of the mobile device 131, and/or one or more modules illustrated in FIG. 6) may execute the set of instructions to perform the process illustrated in FIG. 9. The operations of the illustrated process presented below are intended to be illustrative. In some embodiments, the process illustrated in FIG. 9 may be accomplished with one or more additional operations not described and/or without one or more of the operations discussed. Additionally, the order of the operations of the process illustrated in FIG. 9 and described below is not intended to be limiting.

In 902, the processing device (e.g., the calculation module 520 of the processing device 140) may determine position deviations of first measured flood-field images relative to a center of an EPID (e.g., the EPID 113). The determined position deviations may be used to determine the position offset value. As used herein, the measured flood-field image may refer to a portal image measured (or acquired) by the EPID 113 with the flood field. For example, the flood-field image may be acquired while irradiating the EPID 113 with an open field of 35×35 $cm^2$. The flood field needs to be large enough to cover the entire sensitive area of the detectors in the EPID 113. For example, each first measured flood-field image is a flood-field image with a 10×10 $cm^2$ field when the sensitive area of all the detectors in the EPID 113 is ***.

In some embodiments, the size of an opening or aperture of a beam limiting component (e.g., jaws or MLC) of the treatment head 116 may be adjusted to obtain a large open field. The radiation beams can reach the EPID 113 through the opening of the beam limiting component. The large open field can be called the flood field. The flood-field image can be measured by the EPID 113 with the flood field. In some cases, assembly errors of the treatment head 116 and the EPID 113 may result in a misalignment of the centers of the radiation beams and a flat panel imager of the EPID 113. To resolve the misalignment, in some embodiments, the processing device may determine the position deviations of the measured flood-field image(s) relative to the EPID 113.

Merely by way of example, the EPID 113 includes a flat panel imager with 1024×1024 pixels, and the dimension of the measured flood-field image is 1024×1024 pixels, as well. A pixel grey-scale value of the measured flood-field image may be indicative of an incident radiation dose value. The coordinates of the center of the EPID 113 is (512, 512). In some embodiments, the center of the measured portal image may be aligned to the center of the EPID 113 by calibrating the position deviations between them as exemplified below.

In some embodiments, the EPID 113 may be configured to acquire the first flood-field images with a 10×10 cm² field at collimator angles of 0° and 180°, respectively. For example, the MLC of the treatment head 116 may be positioned at 0° and 180°, respectively. The flood field of 10×10 cm² may be set through the beam limiting component (e.g., opening the jaws). The treatment head 116 may deliver radiations onto the EPID 113. The EPID 113 may measure the first flood-field images corresponding to the collimator angle of 0° and 180°, respectively. In an isocenter plane, Crossline, a dose curve indicative of the dose that is perpendicular to the movement direction of the treatment table and passes through the center of the beam, may be measured. Inline, a dose curve indicative of the dose that is along the movement direction of the treatment table and passes through the center of the beam, may be measured. In some embodiments, the processing device may determine position deviations of the centers of the Crossline and Inline relative to the center of the flat panel imager of the EPID 113. The position deviations may be used to determine the position offset value of the measured portal image relative to the EPID 113. The position offset value, ($\Delta x$, $\Delta y$), may be determined as follows:

$$\Delta x = (xcenter\_collimator0 + xcenter\_collimator180)/2, \quad (6)$$

$$\Delta y = (ycenter\_collimator0 + ycenter\_collimator180)/2, \quad (7)$$

where xcenter_collimator0 represents a position deviation of the center of Crossline relative to the center of the flat panel imager at collimator angle of 0°, xcenter_collimator180 represents a position deviation of the center of Crossline relative to the center of the flat panel imager at collimator angle of 180°, ycenter_collimator0 represents a position deviation of the center of Inline relative to the center of the flat panel imager at collimator angle of 0°, and ycenter_collimator180 represents a position deviation of the center of Inline relative to the center of the flat panel imager at collimator angle of 180°.

In some embodiments, the position offset value may be determined in advance according to Equations 6 and 7. The position offset value may be used to calibrate the measured portal image. For example, the calculation module 520 may align the centers of the measured portal image and the EPID 113 based on the determined position offset value.

In 904, the processing device (e.g., the calculation module 520 of the processing device 140) may determine the detector gain value based on a second measured flood-field image and a beam profile value.

In some embodiments, the second measured flood-field image may be acquired by the EPID 113. The second measured flood-field image may be divided to a series of concentric rings. The beam profile value may be equal to an average of pixel values of the series of concentric rings. The detector gain value may be used to eliminate the sensitivity difference of the detectors of the EPID 113 for the particles of different energies.

Merely by way of example, the EPID 113 may be configured to acquire the second measured flood-field image with a 10×10 cm² at SID=100 cm. The SID may refer to a distance between a radiation source (e.g., the target) of the treatment head 116 to the flat panel imager of the EPID 113. For example, the SID may be set as 100 cm by adjusting positions of the treatment head 116 and the EPID 113. The flood field of 40×40 cm² may be set through the beam limiting component (e.g., opening the jaws). The treatment head 116 may deliver radiations onto the EPID 113. The EPID 113 may acquire the second flood-field image, that is, the second measured flood-field image. The processing device may divide the second measured flood-field image into a series of concentric rings. The processing device may determine an average of pixel values of the series of concentric rings. The beam profile value may be equal to the average. Theoretically, a radiation beam is center-symmetrical with respect to its central axis. Therefore, the dose distributions in the concentric rings may be equal.

In some embodiments, the processing device may determine the detector gain value by dividing the second measured flood-field image by the beam profile value. For example, detector_gain_value=Flood Raw Image/Beam Profile, where "Flood Raw Image" represents image data of the second measured flood-field image, and "Beam Profile" represents the beam profile value. The image data may be a matrix, and each element of the matrix is a value of a pixel of the second measured flood-field image. In some embodiments, the processing device may divide the measured portal image by the detector gain value in order to calibrate the measured portal image.

In some embodiments, the processing device may determine the detector gain value by dividing the beam profile value by the second measured flood-field image. For example, detector_gain_value=Beam Profile/Flood Raw Image. In some embodiments, the processing device may multiply the measured portal image by the detector gain value in order to calibrate the measured portal image.

In some embodiments, the number (or count) of the concentric rings may be various, and not be limited to what are exemplified herein. It is understood that, the more the number (or count) of concentric rings and the smaller a width of each ring, the more accurate the detector gain value.

In some embodiments, operation 902 and operation 904 may be performed simultaneously or sequentially. For example, in operation 904, before determining the beam profile value, the centers of the second measured flood-field image and the EPID 113 may be aligned through the determined position offset value.

In 906, the processing device (e.g., the calculation module 520 of the processing device 140) may determine the curve correction value based on a third measured flood-field image and a predicted flood-field image.

In some embodiments, the curve correction curve may be in the form of a matrix, such as the curve correction matrix. The curve correction matrix may be used to eliminate the over-response of the detectors of the EPID 113 for the particles of low energy. In some embodiments, the third measured flood-field image may be determined based on the second measured flood-field image, the position offset, and the detector gain value. For example, the second measured flood-field image may be aligned to the center of the EPID 113 to form an intermediate flood-field image. The third measured flood-field image may be determined by dividing the intermediate flood-field image by the detector gain value.

In some embodiments, the predicted flood-field image may be a simulated or calculated flood-field image generated by a second portal dose prediction model. The second portal dose prediction model may include an MC simulation model (e.g., a virtual source model) similar to the first portal dose prediction model. Compared with the first portal dose prediction model, the opening size of the beam limiting component (e.g., the jaws or the MCL) modeled in the second portal dose prediction model may be different, and accordingly the field size of the open field may be different as well.

Merely for illustration, in the second portal dose prediction model, the open field may be equal to 40×40 cm², and the SID may be set as 100 cm.

In some embodiments, the processing device may determine the curve correction value by dividing the predicted flood-field image by the third measured flood-field image. For example, curve_correction=Flood Calculated Image/Flood Raw Image, where curve_correction represents the curve correction value, "Flood Calculated Image" represents the predicted flood-field image, and "Flood Raw Image" represents the third measured flood-field image. In some embodiments, the processing device may multiply the measured portal image by the curve correction value in order to calibrate the measured portal image.

In some embodiments, the processing device may determine the curve correction value may be determined by dividing the third measured flood-field image by the predicted flood-field image. For example, curve_correction=Flood Raw Image/Flood Calculated Image. In some embodiments, the processing device may divide the measured portal image by the curve correction value in order to calibrate the measured portal image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 902 and operation 904 may be performed independently. In other words, the position offset value and the detector gain value may be determined, respectively.

Figure 10:
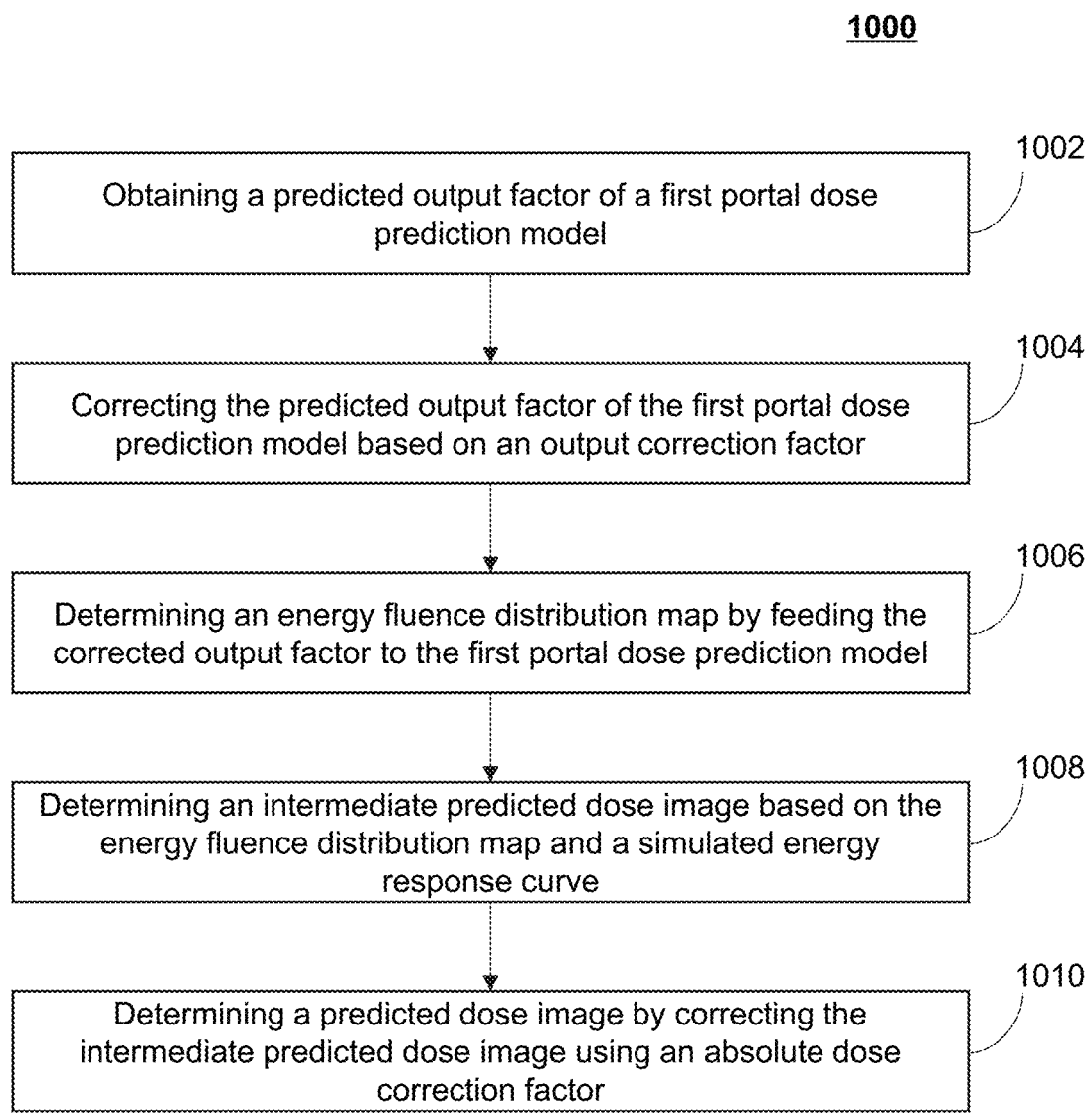
FIG. 10 is a flowchart illustrating an exemplary process for determining a predicted dose image according to some embodiments of the present disclosure.

FIG. 10 is a flowchart illustrating an exemplary process for determining a predicted dose image according to some embodiments of the present disclosure. The predicted dose image may be used to measure radiation delivery errors between the actual radiation delivery and the planned radiation delivery. In some embodiments, the process 1000 may be executed by the medical system 100. For example, the process 1000 may be implemented as a set of instructions (e.g., an application) stored in a storage device (e.g., the storage device 150, the storage 320, and/or the storage unit 490). In some embodiments, the processing device 140 (e.g., the processor 310 of the computing device 300, the CPU 440 of the mobile device 131, and/or one or more modules illustrated in FIG. 6) may execute the set of instructions to perform the process 1000. The operations of the illustrated process presented below are intended to be illustrative. In some embodiments, the process 1000 may be accomplished with one or more additional operations not described and/or without one or more of the operations discussed. Additionally, the order of the operations of the process 1000 illustrated in FIG. 10 and described below is not intended to be limiting.

In 1002, the processing device (e.g., the acquisition module 510 of the processing device 140) may obtain a predicted output factor of a first portal dose prediction model. The first portal dose prediction model may be the MC simulation model (or the virtual source model) described with reference to FIG. 7. The first portal dose prediction model may be model the whole LINAC head geometry (e.g., the treatment head 116) and simulate the radiation delivery of the LINAC (e.g., particle transport between the treatment head 116 and the EPID 113). In some embodiments, the output factor of electron beams is an important parameter for radiation dose calculation. The predicted output factor (also referred to as calculated output factor) may be calculated using the MC simulation. For example, the processing device 140 may calculate the output factor of the delivered electron beams simulated by the virtual source model using the MC dose calculation algorithm. In some cases, due to the difference in energy response for an ionization chamber and the EPID 113, the predicted output factor and the measured output factor may be different. Therefore, the predicted output factor needs to be corrected based on an output correction factor.

In 1004, the processing device (e.g., the calculation module 520 of the processing device 140) may correct the predicted output factor of the first dose prediction model based on an output correction factor. In some embodiments, the processing device may obtain the output correction factor by looking up an output correction factor table. The output correction factor table may be determined in advance based on ratios of predicted output factors to measured output factors for different square fields. For instance, the output correction factor table may be determined, maintained, and/or updated by the manufacturer of the RT apparatus, a vendor that is responsible for maintaining the RT apparatus, etc.; the manufacturer or the vendor may load the output correction factor table may be determined on a storage device (e.g., the storage device 150, the storage module 530, or an external storage device that the medical system 100 or a portion thereof (the processing device 140) may access).

In some embodiments, a virtual source model may be constructed. The SID of the virtual source model may be set as 100 cm. The description regarding the virtual source model may be found in the description with reference with FIG. 7, and is not repeated here.

In some embodiments, the processing device may initial all output correction factors in the output correction factor table. For example, the output correction factors may be initialized to 1. In some embodiments, the processing device may invoke the virtual source model to calculate the predicted output factors for a sequence of square fields. In some embodiments, the processing device may obtain the measured output factors for the sequence of square fields. The measured output factors may be acquired by the EPID 113. For example, the EPID 113 may acquire portal images for the sequence of square fields. The output factors corresponding to the portal images may be measured. In some embodiments, the portal images may be calibrated based on the one or more calibration parameters (e.g., the position offset value, the detector gain value and the curve correction value). The measured output factors may be determined based on the calibrated portal images. In some embodiments, for each of the sequence of square fields, the processing device may determine a ratio of the measured output factor to the predicted output factor. The ratio may be designate as the output correction factor. The output correction factors for different square fields may be recorded in a data table (i.e., the output correction factor table). Through looking up the output correction factor table, the processing device 140 may quickly obtain an output correction factor corresponding to a specific square field. The obtained output correction factor may be used to correct the predicted output factor of the first portal dose prediction model.

In 1006, the processing device (e.g., the calculation module 520 of the processing device 140) may determine an energy fluence distribution map by feeding the corrected output factor to the first portal dose prediction model. The energy fluence distribution map may characterize particles distribution irradiated onto the plane of the EPID 113.

In 1008, the processing device (e.g., the calculation module 520 of the processing device 140) may determine an intermediate predicted dose image based on the energy fluence distribution map and a simulated energy response curve. As described in connection with FIG. 7, the simulated energy response curve (e.g., the simulated energy response curve illustrated in FIG. 11) related to the EPID 113 may be determined by simulating an energy deposition efficiency of the EPID 113. The processing device may multiple the energy fluence distribution map by the simulated energy response curve to determine the intermediate predicted dose image.

In 1010, the processing device (e.g., the calculation module 520 of the processing device 140) may determine a predicted dose image by correcting the intermediate predicted dose image using an absolute dose correction factor. The predicted dose image may be indicative of a dose distribution of the radiation beams calculated or predicted by the first portal dose prediction model.

In some embodiments, the use of the absolute dose correction factor may facilitate to unify units (e.g., pixel values) of the predicted portal dose image and the measured portal dose image. In some embodiments, the absolute dose correction factor may be determined based on a predicted flood-field image and a measured flood-field image. For example, the processing device 140 may obtain the predicted flood-field image with 10×10 cm² field generated by the second portal dose prediction model. The processing device 140 may obtain the measured flood-field image acquired by the EPID 113 with the same field size. The processing device 140 may select a first image patch of 16×16 pixels centered in the predicted flood-field image. The average of pixel values of the first image patch may be designated as a predicted dose of the predicted flood-field image. The processing device 140 may select a second image patch of 16×16 pixels centered in the measured flood-field image. The average of voxel values of the second image patch may be designated as a measured dose of the measured flood-field image. The processing device 140 may determine a ratio of the measured dose to the predicted dose. The determined ratio may be designated as the absolute dose correction factor. In some embodiments, the processing device 140 may multiply the intermediate predicted dose image by the absolute dose correction factor in order to form the predicted dose image and unify the units of the predicted dose image and the measured dose image.

In some embodiments, the processing device may determine a ratio of the predicted dose to the measured dose. The determined ratio may be designated as the absolute dose correction factor. In some embodiments, the processing device 140 may divide the intermediated predicted dose image by the absolute dose correction factor in order to form the predicted dose image and unify the units of the predicted dose image and the measured dose image.

In some embodiments, the absolute dose correction factor may be used to correct the measured dose image. For example, the absolute dose correction factor is equal to the ratio of the measured dose to the predicted dose. In some embodiments, the processing device 140 may divide the measured dose image by the absolute dose correction factor in order to unify the units of the predicted dose image and the measured dose image.

In some embodiments, a reference dose image may be used to unify the units of the predicted dose image and the measured dose image. The reference dose image may be a normalized dose image acquired by the EPID 113. For example, a first absolute dose correction factor may be determined by comparing the measured flood-field image and the reference dose image. A second absolute dose correction factor may be determined by comparing the predicted flood-field image and the reference dose image. The first absolute dose correction factor may be used to correct the measured dose image. The second dose correction factor may be used to correct the predicted dose image. The units of the predicted dose image and the measured dose image may be unified through the correction of the first and second absolute correction factors.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 1002 and operation 1004 may be integrated into a single operation. As another example, operation 1008 and operation 1010 may be integrated into a single operation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment," "one embodiment," or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 1703, Perl, COBOL 1702, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a software as a service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for verifying a predetermined treatment plan, comprising:
    at least one storage device including a set of instructions; and
    at least one processor configured to communicate with the at least one storage device, wherein when executing the set of instructions, the at least one processor is configured to direct the system to perform operations including:
        determining a measured dose image through an electronic portal dose imaging device (EPID), the measured dose image indicating a dose distribution of radiation beams measured by the EPID during a scan that is performed with no patient according to the predetermined treatment plan before a radiation therapy is delivered, and the measured radiation beams corresponding to a planned radiation dose and a planned gantry angle;
        determining an energy fluence distribution map related to radiation beams predicted by a first portal dose prediction model, the predicted radiation beams corresponding to the planned radiation dose and the planned gantry angle;
        determining a predicted dose image based on the energy fluence distribution map and a simulated energy response curve related to the EPID, the predicted dose image indicating a dose distribution of the predicted radiation beams; and
        verifying the predetermined treatment plan by determining differences between the measured dose image and the predicted dose image by comparing the dose distributions of the measured dose image and the predicted dose image.

2. The system of claim 1, wherein the determining a measured dose image includes:
    obtaining a plurality of raw images with respect to the measured radiation beams through the EPID;
    obtaining one or more calibration parameters;
    calibrating, based on the one or more calibration parameters, each of the plurality of raw images;
    forming a final calibrated image based on the plurality of calibrated raw images; and
    converting the final calibrated image to the measured dose image.

3. The system of claim 1, wherein the determining a measured dose image includes:
    obtaining a plurality of raw images with respect to the measured radiation beams through the EPID;
    obtaining one or more calibration parameters;
    summarizing the plurality of raw images;
    forming a final calibrated image by calibrating, based on the one or more calibration parameters, the summarized raw image; and
    converting the final calibrated image to the measured dose image.

4. The system of claim 3, wherein the one or more calibration parameters include at least one of a position offset value, a detector gain value, or a curve correction value.

5. The system of claim 4, wherein the at least one processor is further configured to direct the system to perform the operations including:
    determining the position offset value based on position deviations of first measured flood-field images relative to a center of the EPID;
    determining the detector gain value based on a second measured flood-field image and a beam profile value; and
    determining the curve correction value based on a third measured flood-field image and a predicted flood-field image, wherein the third measured flood-field image is associated with the second measured flood-field image, and the predicted flood-field image is generated using a second portal dose prediction model.

6. The system of claim 5, wherein the first portal dose prediction model or the second portal dose prediction model includes a Monte Carlo (MC) simulation model.

7. The system of claim 1, wherein the determining an energy fluence distribution map related to radiation beams predicted by a first portal dose prediction model includes:
    correcting a predicted output factor of the first portal dose prediction model based on an output correction factor; and
    determining the energy fluence distribution map by feeding the corrected output factor to the first portal dose prediction model.

8. The system of claim 7, wherein the determining a predicted dose image based on the energy fluence distribution map and a simulated energy response curve related to the EPID includes:
    determining an intermediate predicted dose image based on the energy fluence distribution map and the simulated energy response curve; and
    determining the predicted dose image by correcting the intermediate predicted dose image using an absolute dose correction factor.

9. The system of claim 1, wherein the simulated energy response curve related to the EPID is determined in advance by modeling an energy deposition efficiency of the EPID.

10. A method for verifying a predetermined treatment plan implemented on a computing device having at least one processor and at least one storage device, comprising:
    determining a measured dose image through an electronic portal dose imaging device (EPID), the measured dose image indicating a dose distribution of radiation beams measured by the EPID during a scan that is performed with no patient according to the predetermined treatment plan before a radiation therapy is delivered, and the measured radiation beams corresponding to a planned radiation dose and a planned gantry angle;
    determining an energy fluence distribution map related to radiation beams predicted by a first portal dose prediction model, the predicted radiation beams corresponding to the planned radiation dose and the planned gantry angle;
    determining a predicted dose image based on the energy fluence distribution map and a simulated energy response curve related to the EPID, the predicted dose image indicating a dose distribution of the predicted radiation beams; and
    verifying the predetermined treatment plan by determining differences between the measured dose image and the predicted dose image by comparing the dose distributions of the measured dose image and the predicted dose image.

11. The method of claim 10, wherein the determining a measured dose image includes:
    obtaining a plurality of raw images with respect to the measured radiation beams through the EPID;
    obtaining one or more calibration parameters;
    calibrating, based on the one or more calibration parameters, each of the plurality of raw images;
    forming a final calibrated image based on the plurality of calibrated raw images; and
    converting the final calibrated image to the measured dose image.

12. The method of claim 10, wherein the determining a measured dose image includes:
    obtaining a plurality of raw images with respect to the measured radiation beams through the EPID;
    obtaining one or more calibration parameters;
    summarizing the plurality of raw images;
    forming a final calibrated image by calibrating, based on the one or more calibration parameters, the summarized raw image; and
    converting the final calibrated image to the measured dose image.

13. The method of claim 12, wherein the one or more calibration parameters include at least one of a position offset value, a detector gain value, or a curve correction value.

14. The method of claim 13, further comprising:
    determining the position offset value based on position deviations of first measured flood-field images relative to a center of the EPID;
    determining the detector gain value based on a second measured flood-field image and a beam profile value; and
    determining the curve correction value based on a third measured flood-field image and a predicted flood-field image, wherein the third measured flood-field image is associated with the second measured flood-field image, and the predicted flood-field image is generated using a second portal dose prediction model.

15. The method of claim 14, wherein the first portal dose prediction model or the second portal dose prediction model includes a Monte Carlo (MC) simulation model.

16. The method of claim 10, wherein the determining an energy fluence distribution map related to radiation beams predicted by a first portal dose prediction model includes:
    correcting a predicted output factor of the first portal dose prediction model based on an output correction factor; and
    determining the energy fluence distribution map by feeding the corrected output factor to the first portal dose prediction model.

17. The method of claim 16, wherein the determining a predicted dose image based on the energy fluence distribution map and a simulated energy response curve related to the EPID includes:
    determining an intermediate predicted dose image based on the energy fluence distribution map and the simulated energy response curve; and
    determining the predicted dose image by correcting the intermediate predicted dose image using an absolute dose correction factor.

18. The method of claim 10, wherein the simulated energy response curve related to the EPID is determined in advance by modeling an energy deposition efficiency of the EPID.

19. A non-transitory computer-readable medium, comprising at least one set of instructions, wherein when executed by at least one processor of a computer device, the at least one set of instructions directs the at least one processor to perform operations including:
    determining a measured dose image through an electronic portal dose imaging device (EPID), the measured dose image indicating a dose distribution of radiation beams measured by the EPID during a scan that is performed with no patient according to the predetermined treatment plan before a radiation therapy is delivered, and the measured radiation beams corresponding to a planned radiation dose and a planned gantry angle;
    determining an energy fluence distribution map related to radiation beams predicted by a first portal dose prediction model, the predicted radiation beams corresponding to the planned radiation dose and the planned gantry angle;

determining a predicted dose image based on the energy fluence distribution map and a simulated energy response curve related to the EPID, the predicted dose image indicating a dose distribution of the predicted radiation beams; and verifying the predetermined treatment plan by determining differences between the measured dose image and the predicted dose image by comparing the dose distributions of the measured dose image and the predicted dose image.

20. The non-transitory computer-readable medium of claim 19, wherein the first portal dose prediction model includes a Monte Carlo (MC) simulation model.

* * * * *